United States Patent
Houlihan et al.

(10) Patent No.: US 12,315,616 B1
(45) Date of Patent: May 27, 2025

(54) SYSTEMS AND METHODS FOR A SPATIAL QUANTITATIVE AND ANATOMICALLY ACCURATE SURGICAL CORRIDOR MODELING PLATFORM

(71) Applicant: Dignity Health, San Francisco, CA (US)

(72) Inventors: Lena Mary Houlihan, San Francisco, CA (US); David Naughton, San Francisco, CA (US); Mark Preul, San Francisco, CA (US)

(73) Assignee: Dignity Health, San Francisco, CA (US)

( * ) Notice: Subject to any disclaimer, the term of this patent is extended or adjusted under 35 U.S.C. 154(b) by 235 days.

(21) Appl. No.: 17/738,273

(22) Filed: May 6, 2022

Related U.S. Application Data

(60) Provisional application No. 63/185,081, filed on May 6, 2021.

(51) Int. Cl.

| | |
|---|---|
| *G16H 20/40* | (2018.01) |
| *A61B 34/10* | (2016.01) |
| *G06T 17/30* | (2006.01) |
| *G06T 19/00* | (2011.01) |
| *G06T 19/20* | (2011.01) |

(52) U.S. Cl.
CPC ............ *G16H 20/40* (2018.01); *A61B 34/10* (2016.02); *G06T 17/30* (2013.01); *G06T 19/003* (2013.01); *G06T 19/20* (2013.01); *A61B 2034/104* (2016.02); *A61B 2034/105* (2016.02); *A61B 2034/107* (2016.02); *G06T 2210/41* (2013.01); *G06T 2219/2004* (2013.01)

(58) Field of Classification Search
CPC .. G16H 20/40; A61B 34/10; A61B 2034/104; A61B 2034/105; A61B 2034/107; G06T 17/30; G06T 19/003; G06T 19/20; G06T 2210/41; G06T 2219/2004
See application file for complete search history.

(56) References Cited

U.S. PATENT DOCUMENTS

| | | | |
|---|---|---|---|
| 2001/0002310 A1* | 5/2001 | Chishti | A61C 7/08 345/20 |
| 2013/0345718 A1* | 12/2013 | Crawford | A61B 90/39 606/130 |
| 2017/0258526 A1* | 9/2017 | Lang | A61B 17/1775 |
| 2021/0264601 A1* | 8/2021 | Pasha | G06F 18/22 |
| 2022/0117667 A1* | 4/2022 | Liu | A61B 34/20 |
| 2023/0044706 A1* | 2/2023 | Frisken | A61B 34/10 |
| 2023/0149091 A1* | 5/2023 | Cohen-Gadol | G06T 15/08 606/1 |

* cited by examiner

*Primary Examiner* — Hien N Nguyen
(74) *Attorney, Agent, or Firm* — Polsinelli PC

(57) ABSTRACT

Various embodiments of a system and associated method for modeling an average surgical corridor based on a plurality of datasets are disclosed herein.

9 Claims, 26 Drawing Sheets

200

210 TRANSLATE DATA FOR EACH SELECTED DATASET OF A PLURALITY OF SELECTED DATASETS FROM A FIRST 3D COORDINATE SYSTEM TO A STANDARDIZED SECOND 3D COORDINATE SYSTEM

220 DETERMINE AVERAGE CENTRAL AXIS LINE $L_{AVG}$ AND ASSOCIATED AVERAGE PERPENDICULAR PLANE $P_{AVG}$ FOR THE PLURALITY OF SELECTED DATASETS BASED ON INDIVIDUAL CENTROID LINES $L_C$ ASSOCIATED WITH A PLURALITY OF ORIGINAL CORRIDOR POINTS $C_1$-$C_m$ FOR EACH RESPECTIVE SELECTED DATASET

230 TRANSLATE ALL ORIGINAL CORRIDOR POINTS $C_1$-$C_m$ FROM EACH SELECTED DATASET TO AVERAGE PERPENDICULAR PLANE $P_{AVG}$ TO GENERATE TRANSLATED CORRIDOR POINTS $C_1'$-$C_m'$

240 FOR EACH SELECTED DATASET GENERATE CORRIDOR INTERSECTION POINTS $D_1$-$D_N$ AT EQUIDISTANT RADIAL VECTORS $V_1$-$V_N$ TO DESCRIBE CORRIDOR SHAPE BY FITTING A SPLINE CURVE $S_P$ TO TRANSLATED CORRIDOR POINTS $C_1'$-$C_m'$ AND GENERATING CORRIDOR INTERSECTION POINTS $D_1$-$D_N$ THAT FIT SPLINE CURVE $S_P$

250 GENERATE AVERAGE SURGICAL CORRIDOR $C_{VSF\_AVG}$ BY AVERAGING SHAPE OF SURGICAL CORRIDOR $C_{VSF}$ AND TARGET STRUCTURE $T_1$ FOR EACH SELECTED DATASET, WHERE SURGICAL CORRIDOR $C_{VSF}$ IS DETERMINED FOR EACH SELECTED DATASET USING CORRIDOR INTERSECTION POINTS $D_1$-$D_N$ AT EQUIDISTANT RADIAL VECTORS $V_1$-$V_N$

260 SUPERIMPOSE MODEL OF AVERAGE SURGICAL CORRIDOR $C_{VSF\_AVG}$ ON PATIENT IMAGING

210 — TRANSLATE DATA FOR EACH SELECTED DATASET OF A PLURALITY OF SELECTED DATASETS FROM A FIRST 3D COORDINATE SYSTEM TO A STANDARDIZED SECOND 3D COORDINATE SYSTEM

212 — OBTAIN MEASURED DATA POINTS FOR EACH SELECTED DATASET INCLUDING FIRST REFERENCE POINT $R_1$, SECOND REFERENCE POINT $R_2$, TARGET STRUCTURE REFERENCE POINT $T_1$, AND A PLURALITY OF ORIGINAL CORRIDOR POINTS $C_1$-$C_m$ WITHIN A FIRST 3D COORDINATE SYSTEM

214 — TRANSLATE ALL MEASURED DATA POINTS TO A SECOND 3D COORDINATE SYSTEM SUCH THAT THE TARGET STRUCTURE REFERENCE POINT $T_1$ IS LOCATED AT AN ORIGIN, FIRST AND SECOND REFERENCE POINTS $R_1$ AND $R_2$ ARE LOCATED ON AN XY PLANE, MIDPOINT $R_3$ DEFINED ON A LINE $L_R$ BETWEEN $R_1$ AND $R_2$, AND AN X-AXIS IS ALIGNED ON A LINE $L_X$ JOINING $T_1$ TO MIDPOINT $R_3$

FIG. 6

220 — DETERMINE AVERAGE CENTRAL AXIS LINE $L_{AVG}$ AND ASSOCIATED AVERAGE PERPENDICULAR PLANE $P_{AVG}$ FOR THE PLURALITY OF SELECTED DATASETS BASED ON INDIVIDUAL CENTROID LINES $L_C$ ASSOCIATED WITH THE PLURALITY OF ORIGINAL CORRIDOR POINTS $C_1$-$C_m$ FOR EACH RESPECTIVE SELECTED DATASET

222 — FOR EACH SELECTED DATASET, DETERMINE A CENTROID $C_{SET}$ OF ORIGINAL CORRIDOR POINTS $C_1$-$C_m$ AND DETERMINE CENTROID LINE $L_C$ BETWEEN $C_{SET}$ AND TARGET STRUCTURE $T_1$

224 — DETERMINE AN AVERAGE CENTROID $C_{AVG}$ OF ALL CENTROIDS $C_{SET}$ OF THE PLURALITY OF SELECTED DATASETS AND DETERMINE AVERAGE CENTRAL AXIS LINE $L_{AVG}$ BETWEEN $C_{AVG}$ AND TARGET STRUCTURE $T_1$

226 — DETERMINE AN AVERAGE PERPENDICULAR PLANE $P_{AVG}$ PERPENDICULAR TO AVERAGE CENTRAL AXIS LINE $L_{AVG}$ AT A PREDETERMINED DISTANCE FROM TARGET STRUCTURE $T_1$

FIG. 9

230 — TRANSLATE ALL ORIGINAL CORRIDOR POINTS $C_1$-$C_m$ FROM EACH SELECTED DATASET TO AVERAGE PERPENDICULAR PLANE $P_{AVG}$ TO GENERATE TRANSLATED CORRIDOR POINTS $C_1'$-$C_m'$

232 — DETERMINE VECTOR BETWEEN TARGET STRUCTURE $T_1$ AND EACH ORIGINAL CORRIDOR POINT $C_1$-$C_m$ AND TRANSLATE EACH ORIGINAL CORRIDOR POINT $C_1$-$C_m$ TO THE AVERAGE PERPENDICULAR PLANE $P_{AVG}$ TO BECOME TRANSLATED CORRIDOR POINTS $C_1'$-$C_m'$

234 — DEFINE FIRST 2D COORDINATE SYSTEM ON PERPENDICULAR PLANE $P_{AVG}$ WITH TRANSLATED CORRIDOR POINTS $C_1'$-$C_m'$

240 — FOR EACH SELECTED DATASET GENERATE CORRIDOR INTERSECTION POINTS $D_1$-$D_N$ AT EQUIDISTANT RADIAL VECTORS $V_1$-$V_N$ TO DESCRIBE CORRIDOR SHAPE BY FITTING A SPLINE CURVE $S_P$ TO TRANSLATED CORRIDOR POINTS $C_1'$-$C_m'$ AND GENERATE CORRIDOR INTERSECTION POINTS $D_1$-$D_N$ THAT FIT SPLINE CURVE $S_P$

242 — GENERATE PIECEWISE SPLINE CURVE $S_P$ TO FIT TO TRANSLATED CORRIDOR POINTS $C_1'$-$C_m'$ WHERE EACH SPLINE CURVE SECTION $S_t$ WHERE $t \in \{1,...,m\}$ OF SPLINE CURVE $S_P$ IS DEFINED BY A RESPECTIVE 3$^{RD}$ DEGREE POLYNOMIAL

244 — GENERATE EQUDISTANT RADIAL VECTORS $V_1$-$V_N$ EMANATING FROM CENTROID $C_{SET}$ TO INTERSECT WITH SPLINE CURVE $S_P$

246 — GENERATE CORRIDOR INTERSECTION POINTS $D_1$-$D_N$ AT RESPECTIVE INTERSECTIONS BETWEEN EQUIDISTANT RADIAL VECTORS $V_1$-$V_N$ AND SPLINE CURVE $S_P$

FIG. 15

250 — GENERATE AVERAGE MODEL CORRIDOR $C_{VSF\_AVG}$ BY AVERAGING OUTER SHAPE OF $C_{VSF}$ AND TARGET STRUCTURE $T_1$ FOR EACH SELECTED DATASET

252 — AVERAGE ALL CORRIDOR INTERSECTION POINTS $D_1$-$D_N$ ASSOCIATED WITH RADIAL REFERENCE LINES EQUIDISTANT RADIAL VECTORS $V_1$-$V_N$ FOR ALL SELECTED DATASETS

254 — TRANSLATE AVERAGE CORRIDOR INTERSECTION POINTS $D_{1\_AVG}$-$D_{N\_AVG}$ TO SECOND 3D COORDINATE SYSTEM TO GENERATE AVERAGE MODEL CORRIDOR $C_{VSF\_AVG}$

| 310 | RECEIVE, AT A USER INTERFACE, A QUERY INCLUDING PROCEDURAL INFORMATION REGARDING A PROCEDURE TO BE PERFORMED |
|---|---|
| 320 | RECEIVE, AT THE USER INTERFACE, PATIENT-SPECIFIC INFORMATION REGARDING THE SURGICAL PROCEDURE TO BE PERFORMED |
| 330 | QUERY A DATABASE BASED ON THE PROCEDURAL INFORMATION AND THE PATIENT-SPECIFIC INFORMATION TO IDENTIFY A PLURALITY OF SELECTED DATASETS OF A PLURALITY OF DATASETS STORED WITHIN THE DATABASE |
| 340 | RETRIEVE THE PLURALITY OF SELECTED DATASETS FROM THE DATABASE |
| 350 | CALCULATE THE AVERAGE CORRIDOR BASED ON THE PLURALITY OF SELECTED DATASETS |
| 360 | RETURN VARIOUS METRICS INCLUDING THE AVERAGE NORMALIZED VOLUME OF SURGICAL CORRIDORS |
| 370 | GENERATE A 3D MODEL OF THE AVERAGE CORRIDOR |
| 380 | ALIGN THE 3D MODEL WITH RESPECT TO PATIENT IMAGING |
| 390 | DISPLAY, AT A DISPLAY DEVICE, THE 3D MODEL OF THE AVERAGE CORRIDOR WITH RESPECT TO PATIENT IMAGING |

FIG. 19

SYSTEMS AND METHODS FOR A SPATIAL QUANTITATIVE AND ANATOMICALLY ACCURATE SURGICAL CORRIDOR MODELING PLATFORM

CROSS-REFERENCE TO RELATED APPLICATIONS

This is a U.S. non-provisional patent application that claims benefit to U.S. Provisional Patent Application Ser. No. 63/185,081 filed 6 May 2021, which is herein incorporated by reference in its entirety.

FIELD

The present disclosure generally relates to preoperative modeling, and in particular, to a system and associated method for generating an average surgical model for a surgical corridor from multiple sample sets.

BACKGROUND

Quantitative anatomy is the method by which neurosurgeons assess the surgical benefits and disadvantages of different surgical approaches using surgical technology. The purpose of studying quantitative anatomy is to improve the techniques and approaches used in neurosurgery or other related surgery disciplines. This process allows surgeons and related personnel to assess, plan and select the optimal intervention or surgical approach specific to the pathology, thereby aiming to improve surgical outcomes for patients. The ability to move and manipulate surgical instruments is an integral aspect of selecting an optimal surgical approach or comparing one surgical approach to another. This is especially relevant in neurosurgery, where surgical access through the cranium and into the deep areas of the brain is often restricted. Furthermore, in cases where the procedure is performed using an operating microscope for magnification, movement of surgical instruments to work on pathoanatomic structures may be in terms of millimetric distances.

Brain structure and topology, as well as other structures in the body, can vary significantly across a population with traits such as sex, age, and various conditions. For instance, the brain of a 75 year old male with dementia will be far different in size and shape from that of a 30 year old female without comorbidities, and thus a surgical approach to either individual will need to be examined differently. Thus, during training it is imperative that models be realistic representations of how to surgically access various structures.

It is with these observations in mind, among others, that various aspects of the present disclosure were conceived and developed.

BRIEF DESCRIPTION OF THE DRAWINGS

FIG. 3 is a flowchart showing a method for generating a model of a surgical corridor as performed by the system of FIG. 1A;

FIG. 6 is a flowchart showing substeps of the method of FIG. 3 as illustrated in FIGS. 4 and 5;

FIG. 9 is a flowchart showing substeps of the method of FIG. 3 as illustrated in FIGS. 7 and 8;

FIG. 12 is a flowchart showing substeps of the method of FIG. 3 as illustrated in FIGS. 10 and 11;

FIG. 15 is a flowchart showing substeps of the method of FIG. 3 as illustrated in FIGS. 13 and 14;

FIG. 17 is a flowchart showing substeps of the method of FIG. 3 as illustrated in FIG. 16;

FIG. 19 is a flowchart showing generation of the model of the average surgical corridor by the system of FIG. 1A based on user-provided selections;

Corresponding reference characters indicate corresponding elements among the view of the drawings. The headings used in the figures do not limit the scope of the claims.

DETAILED DESCRIPTION

Figure 1A:
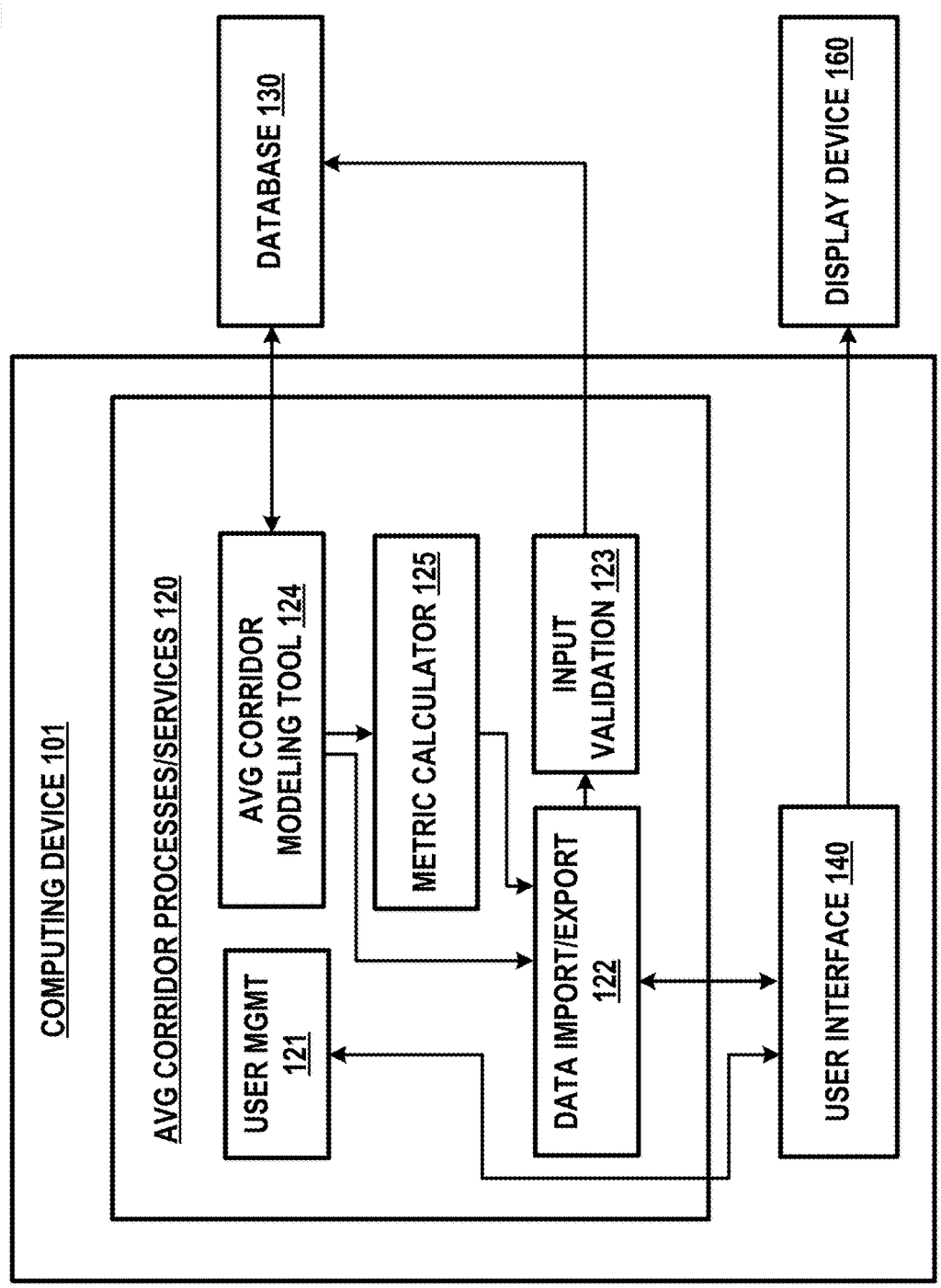
FIG. 1A is a diagram showing a system for generating a model of a surgical corridor and FIG. 1B is a diagram showing aspects of the system of FIG. 1A for populating a database.

Various embodiments of a computer-implemented system and associated method for determining and displaying a model for an average surgical corridor from multiple sample sets are disclosed herein. The system includes a large database of cadaveric measurements that includes information used in creating 3D models of surgical corridors specific to different approaches, maneuvers and structures. To achieve a predictive model for a combination of side, approach, maneuver, and structure, measurements related to this combination can be selected from the database. Using different anatomical information attached to each cadaveric measurement, such as age, sex, cranial volume and parenchymal volume obtained from preclinical imaging (magnetic resonance, computed tomography, ultrasound, or any other imaging modality that can produce volumetric imaging data), a subset of a plurality of datasets can be chosen based on the age, sex, cranial volume, parenchymal and other patient-specific anatomy. Selected datasets are then combined to produce an "average" 3D surgical corridor, which is spatially accurate and spatially oriented and can be superimposed on imaging of the patient's anatomy to produce a predictive 3D surgical corridor for use pre-operatively or intraoperatively.

While one cannot comprehensively quantitatively or qualitatively estimate the affect a lesion has on the intracranial space, or the amount of potential space garnered specific to an approach, the present system allows use of anatomical parameters to refine analysis. CT and MRI, or another imaging modality, can assess the volume of brain parenchyma as well as the volume of the intracranial compartment, i.e. the skull. In this database, the acquired imaging data set allows the measurement of the volume of the intracranial parenchyma, the total intracranial volume and segment the cranium into different compartments (supratentorial, infratentorial etc.). Comparing this with collected cadaveric quantitative data and demographics, the patient's anatomical and radiographic volumetric parameters can be used to predict the volume of surgical freedom (VSF) of surgical target structures relevant to the surgical corridor(s) specific to the patient's cranial anatomy.

In particular, the system is operable for accepting data including a plurality of 3-dimensional locations of various points within a body. Data can be for a plurality of bodies across a plurality of datasets to identify an "average" surgical corridor among the bodies of a selected dataset. This can prove useful when generating specialized "averages" for surgical and anatomical study or planning, such as for an average surgical corridor for a cohort defined alone or singly, or for instance in combination with imaging, image-guided surgical navigation systems, or robotic surgical systems where delineation of the surgical corridor and/or surgical access limitations are defined (e.g., "no fly zones"). Current image-guided surgical systems use a single line to represent the trajectory from the point of entry on the skull to the target of surgical interest. In contrast, the present disclosure describes creation of a model of an average surgical corridor that can be incorporated into an image-guided surgical system such that the trajectory of the approach is not represented by a single line, but is instead presented to the operator as a three dimensional corridor. This average surgical corridor can be used in real time as part of the image guided surgical system to visualize the expected freedom of movement of surgical instruments available to the surgeon.

Referring to FIGS. 1A-5, a surgical corridor modeling system 100 (hereinafter, system 100) provides a computing device 101 that implements various methods for generating a model of an average surgical corridor based on anatomical coordinate data. The computing device 101 includes a plurality of modules, collectively "average surgical corridor processes/services" 120, that communicate with a database 130 that includes anatomical coordinate data for a plurality of datasets, where each dataset corresponds to a respective specimen of a plurality of specimens. In particular, the database 130 receives and stores 3-dimensional positional data for a plurality of datasets; each dataset of the plurality of datasets including a set of measured data points for various reference points within a structure of the body, and each dataset of the plurality of datasets corresponds to a respective specimen of a plurality of specimens. In one embodiment, each dataset includes positional data from various points around a skull and a target structure within the brain on cadaveric specimens. The system 100 combines an anatomical volumetric database such as database 130 with the average surgical corridor processes/services" 120 that perform volumetric imaging analysis to produce a model that can represent a patient's expected anatomical and radiographic volumetric parameters and thus predict a volume of surgical freedom to reach surgical target structures of the respective surgical corridors specific to the patient's cranial anatomy, resulting in quantitative and visual information for pre-operative and intra-operative planning. The system further includes a user interface 140 in communication with a display device 160 for entering information and for viewing the model and patient imaging. In some embodiments, the user interface 140 can be viewed in a web browser.

In some embodiments, the average surgical corridor processes/services 120 receives data from the user interface 140, which can include one or more sets of measured data points for populating the database 130 and can also include selection information indicative of one or more selections received from a user to generate an "expected" surgical corridor based on the selection information. For instance, the average surgical corridor processes/services 120 can receive selection information from a practitioner through the user interface 140 such as a type of procedure to be performed on a living patient, an age range, a surgical approach, a head side, and/or a gender of the patient. The average surgical corridor processes/services 120 can then search the database 130 to identify a plurality of selected datasets which are a subset of the plurality of datasets that correspond to the selection information. Following identification of the plurality of selected datasets, the average surgical corridor processes/services 120 can determine an average surgical corridor and generate a model of the average surgical corridor based on sets of measured data points present in the plurality of selected datasets, and can further calculate a plurality of surgical corridor metrics including normalized volume based on the average surgical corridor. The average surgical corridor processes/services 120 can then communicate with the user interface 140 to display the model of the expected surgical corridor superimposed over patient imaging at the display device 160. This process is elaborated on in further detail herein with reference to FIGS. 18A-19.

As shown, the average surgical corridor processes/services 120 includes a user management module 121 for validating a user and maintaining user profiles. Further, the average surgical corridor processes/services 120 includes a data import/export module 122 in communication with the user interface 140 for importing datasets into the database 130, and an input validation module 123 for ensuring that imported data is properly formatted upon entry into the database 130. The average surgical corridor processes/services 120 provides an average surgical corridor modeling tool 124 that models the average surgical corridor based on the plurality of selected datasets of the plurality of datasets, the average surgical corridor modeling tool 124 retrieves based on the selections received through the user interface 140. The average surgical corridor processes/services 120 can also include a metric calculator 125 that calculates various metrics related to the datasets and the modeled average surgical corridor.

The data import/export module 122 can also export data from the metric calculator 125 and the average surgical corridor modeling tool 124, which can include a model of the average surgical corridor. In some embodiments, the user interface 140 displays the model of the average surgical corridor superimposed over patient imaging at the display device 160 as will be discussed in further detail herein with reference to FIGS. 18A-18D.

Database Population

Figure 1B:
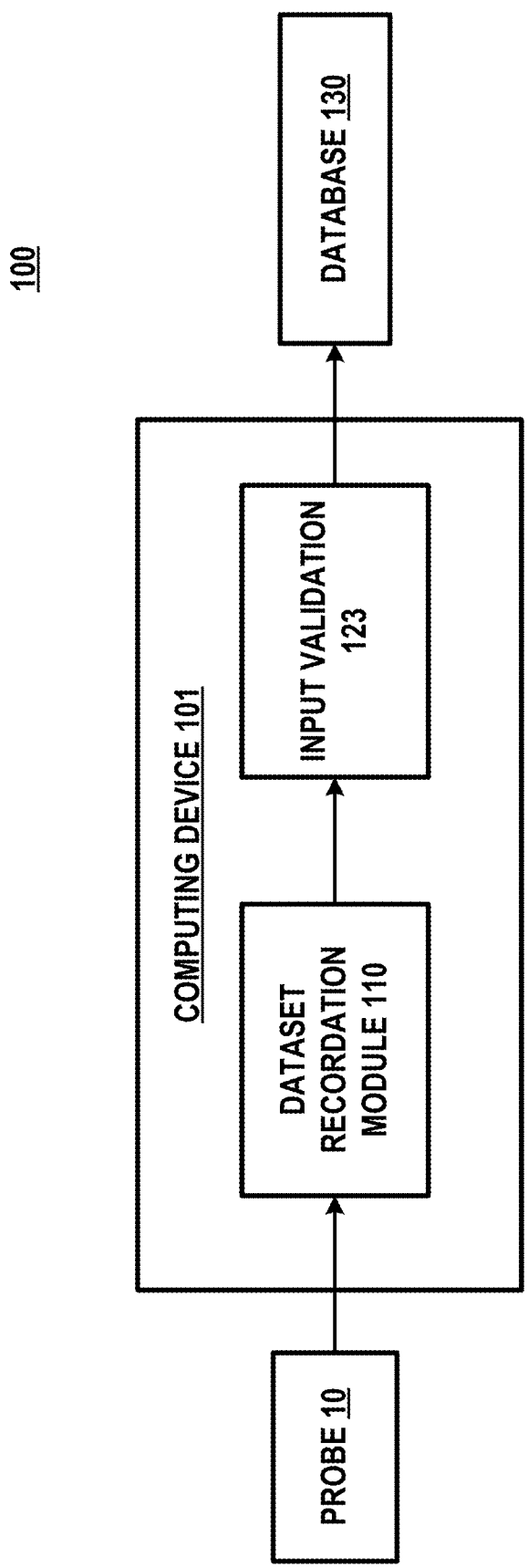
Figure 2:
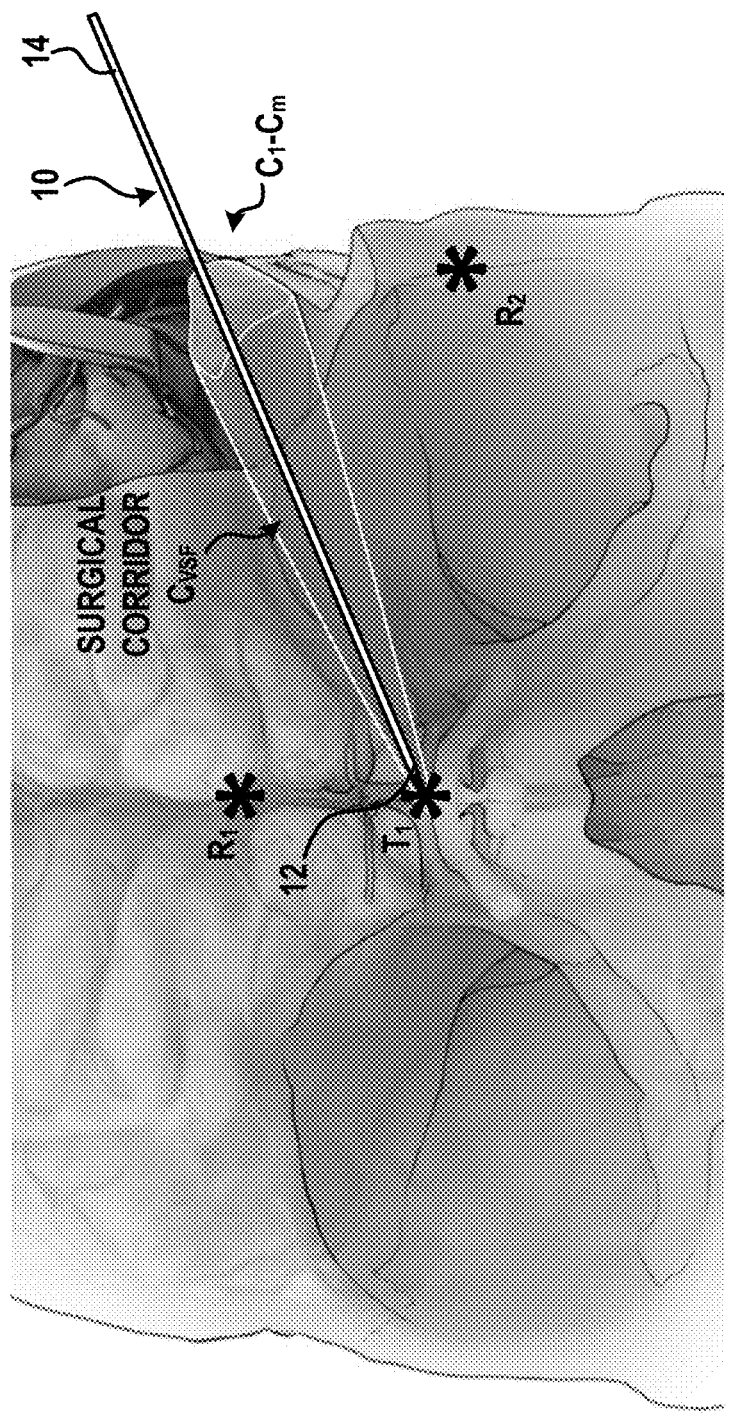
FIG. 2 is an illustration showing an example surgical corridor within a skull.

As shown specifically in FIGS. 1B and 2, to populate the set of measured data points for each dataset within the database 130, 3-D positional coordinates of two reference points $R_1$ and $R_2$ must be recorded for each dataset of the plurality of datasets. In some embodiments, the system 100 can include a dataset recordation module 110 on the computing device 101 in electrical communication with a probe 10 that populates the database 130 with a set of measured data points for each respective dataset of the plurality of datasets, which can be further validated with input validation module 123 that ensures proper formatting of the extracted data points. In one particular embodiment involving cranial surgery, for each dataset corresponding to a respective "head" of a plurality of heads, the system 100 extracts positions of a first reference point $R_1$ at the glabella (right between the eyebrows) and a second reference point $R_2$ at the lateral canthus (lateral edge of the eyelid) by the probe 10. Further, the system 100 measures positional coordinates of a target structure $T_1$ within the body. To enable the system 100 to measure the positional coordinates, a practitioner can place the probe 10 with a distal end 12 of the probe 10 at the target structure $T_1$. Using the probe 10, the system 100 captures a plurality of original corridor points $C_1$-$C_m$ at the skull around a surgical corridor such that the distal end 12 of the probe 10 is still on the target structure $T_1$ and the plurality of original corridor points $C_1$-$C_m$ are at the extrema of the surgical corridor. As such, the set of measured data points obtained by the system 100 for each respective dataset of the plurality of datasets can include positions of the first reference point $R_1$, the second reference point $R_2$, the target structure $T_1$, and the plurality of original corridor points $C_1$-$C_m$. It should be noted that while the discussion herein pertains to target structures within the brain and the plurality of original corridor points are on the skull in the context of cranial surgery, various other bodily structures are contemplated.

Cadaveric measurement data considers the movement of structures during a specific surgical approach, as well as the actions or maneuvers of a surgeon while they are operating. Combining this with patient imaging could provide a more detailed pre-operative picture, which provides the surgeon not only with an anatomical insight specific to the patient and to access the pathology or surgical situation, but also the likely potential space that can be garnered during a specific approach, and the areas and structures that are most likely to be impacted during the approach. This allows for more informed pre-operative approach selection or planning such as with surgical planning systems that may or may not incorporate image guidance or robotically-based surgical systems.

Intraoperatively, the model of the average surgical corridor can be aligned to the patient's imaging dataset and displayed at the display device 160 to produce a graphical guide to safe zones during intra-operative manipulation. This could be used as a visual guide for the surgeon to inform the approach in real time. In some embodiments, the system 100 can flag instances of a surgical instrument moving outside the surgical corridor or safe zone and display an alert at the display device 160 or another suitable output device to inform a practitioner of such an event.

Measurement Data

Figure 4:
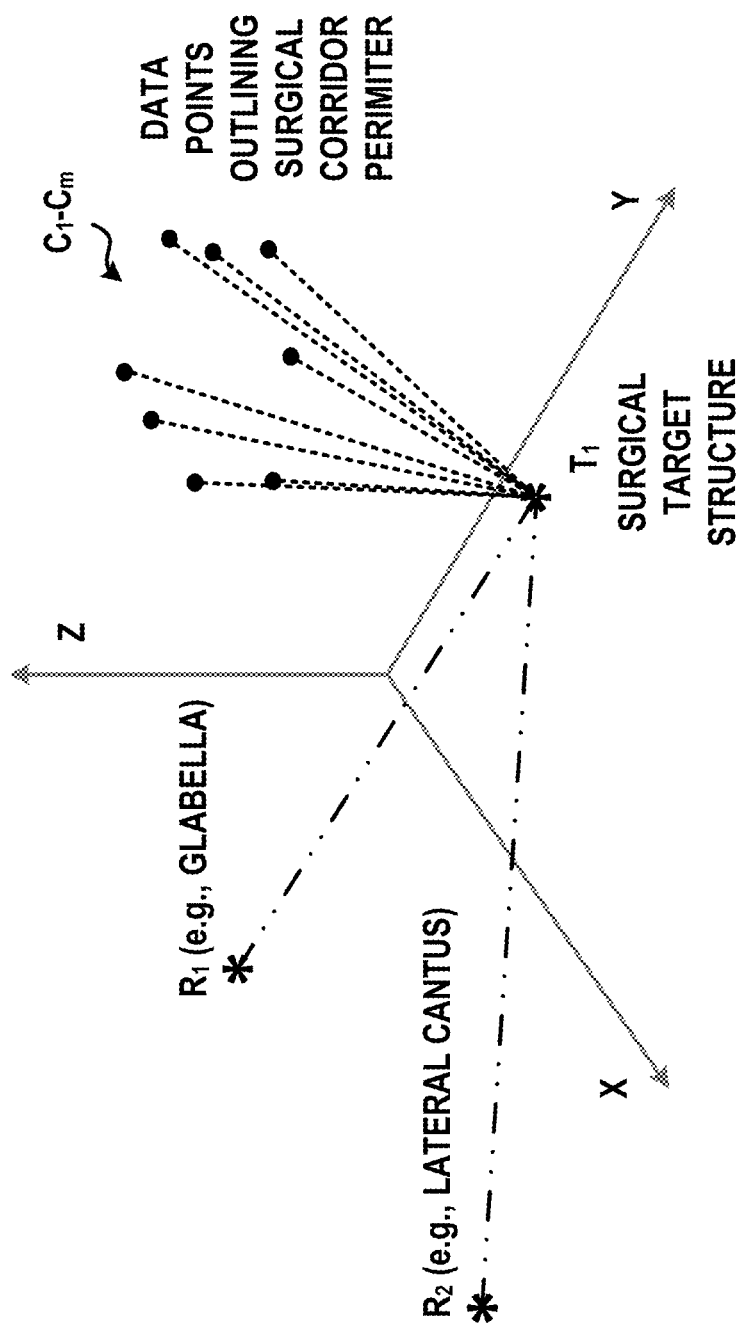
FIG. 4 is a graphical representation showing measured data points including a first reference point, a second reference point, a target structure reference point, and a plurality of corridor points in a first 3D coordinate system according to the method of FIG. 3.

With reference to FIGS. 2-4, the system 100 can obtain the set of measured data points including 3D positional coordinate data of three reference points for all datasets, each dataset corresponding to one specimen of a plurality of specimens and including 3-D coordinates for the following reference points:

Structure of interest (STS) $T_1$
First reference point $R_1$
Second reference point $R_2$ In one embodiment, the first reference point $R_1$ is selected to be the glabella, which is located at a midpoint between the eyebrows and above the nose. The second reference point $R_2$ is selected to be the lateral canthus, which is located at a lateral intersection of the upper eyelid and the lower eyelid.

Reference points $T_1$, $R_1$ and $R_2$ are used to orient the model in 3D space and in relation to other models.

The set of measured data points of each individual dataset of the plurality of datasets further includes the plurality of original corridor points $C_1$-$C_m$ where the plurality of original corridor points $C_1$-$C_m$ are points in 3D space, measured towards a proximal end 14 of the probe 10 with the distal end 12 on the target structure $T_1$, and the probe 10 placed at the extrema of maneuverability in the surgical corridor. Any number of points greater than 3 can be used for the surgical corridor modeling system 100, and the greater the number of points, the more accurate the model will be. One example implementation of this methodology uses m=8 data points $C_1$-$C_8$.

The system 100 can combine sets of measurement data from plurality of selected datasets to produce a model of an "average" 3D surgical corridor, which is spatially accurate and spatially oriented and can be superimposed over imaging of the patient's anatomy to produce a predicted 3D surgical corridor for use pre-operatively or intraoperatively. Orientation points included with cadaveric data can be used to orient the surgical corridor in 3D space, and can allow the superimposition of the model onto the patient's imaging dataset by aligning a small number of these orientation points with the corresponding anatomical features of the patient's imaging. Determination and modeling of the volume of surgical freedom allows the means to produce anatomically and spatially accurate representations of the surgical corridor with respect to the patient's imaging parameters. Further, the model of the surgical corridor can be used to aid surgical planning and can be incorporated into image guided surgical planning systems, stereotactic navigation systems, and/or robotic surgical systems.

It should be noted that any means of 3D volume imaging can be used to generate the dataset and/or to generate patient imaging dataset(s) for superposition of a modeled surgical corridor onto the imaging. Such an imaging dataset can become incorporated as the basis of image guidance or image control for surgical planning systems and/or robotic surgical systems. While the surgical corridor modeling system 100 can use traditional 3D medical imaging such as CT or MRI, the surgical corridor modeling system 100 can also accept data from any medical imaging system, device, instrument, or tool that produces or can be altered to produce a 3D volumetric imaging dataset. For instance, the system 100 can include a 2D dataset that is altered or supplemented to become a 3D volumetric dataset. In some embodiments, the surgical corridor modeling system 100 can be used to superimpose a model of an average surgical corridor on patient imaging at an appropriate location relative to a target structure.

Average Surgical Corridor Derivation

Overview

Figure 5:
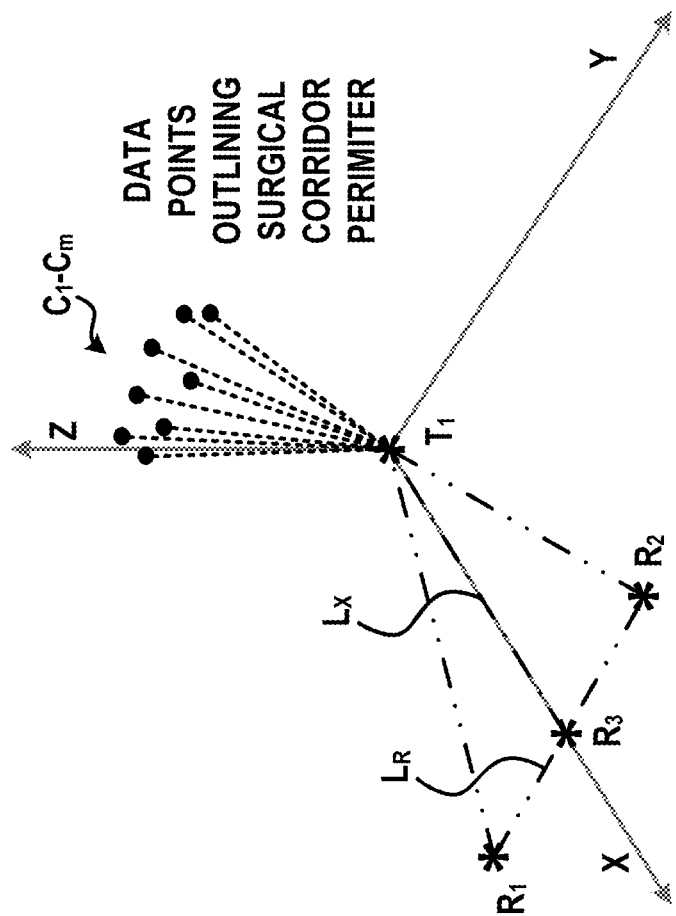
FIG. 5 is a graphical representation showing the measured data points of FIG. 4 including the first reference point, the second reference point, the target structure reference point, and the plurality of corridor points translated to a second 3D coordinate system with the target structure reference point located at a center of the second 3D coordinate system.
Figure 7:
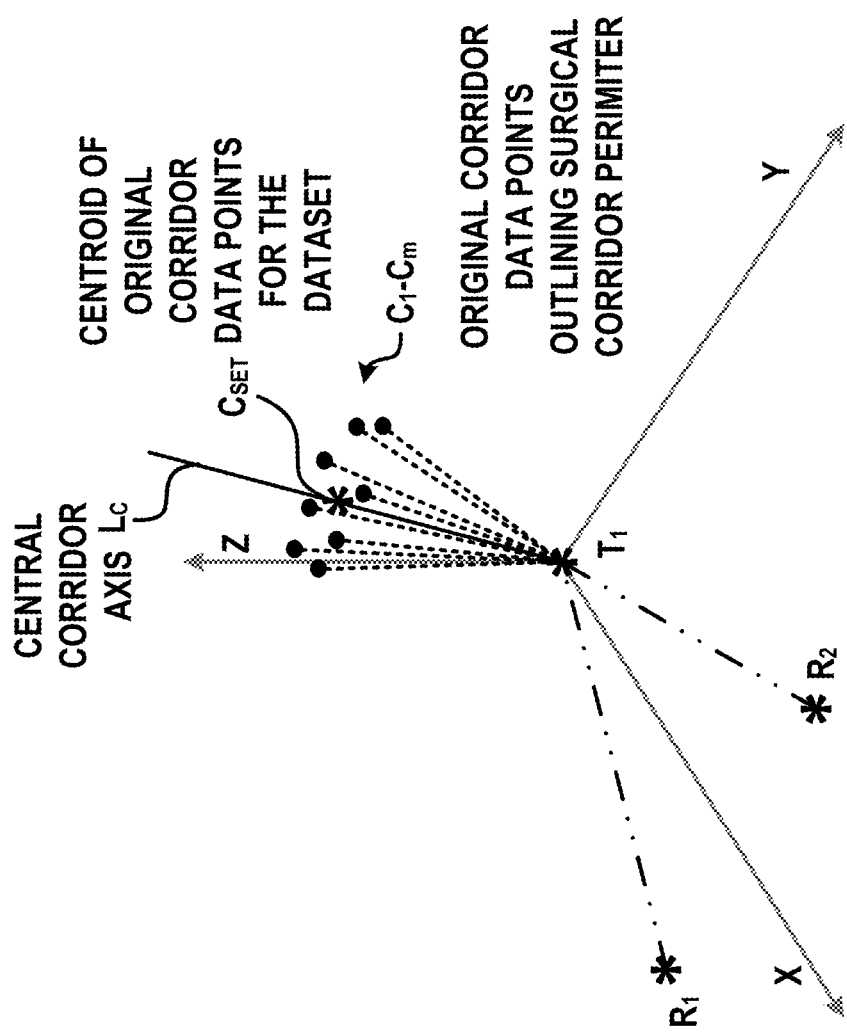
FIG. 7 is a graphical representation showing the measured data points and second 3D coordinate system of FIG. 5 including a centroid corridor line associated with the plurality of corridor points.
Figure 8:
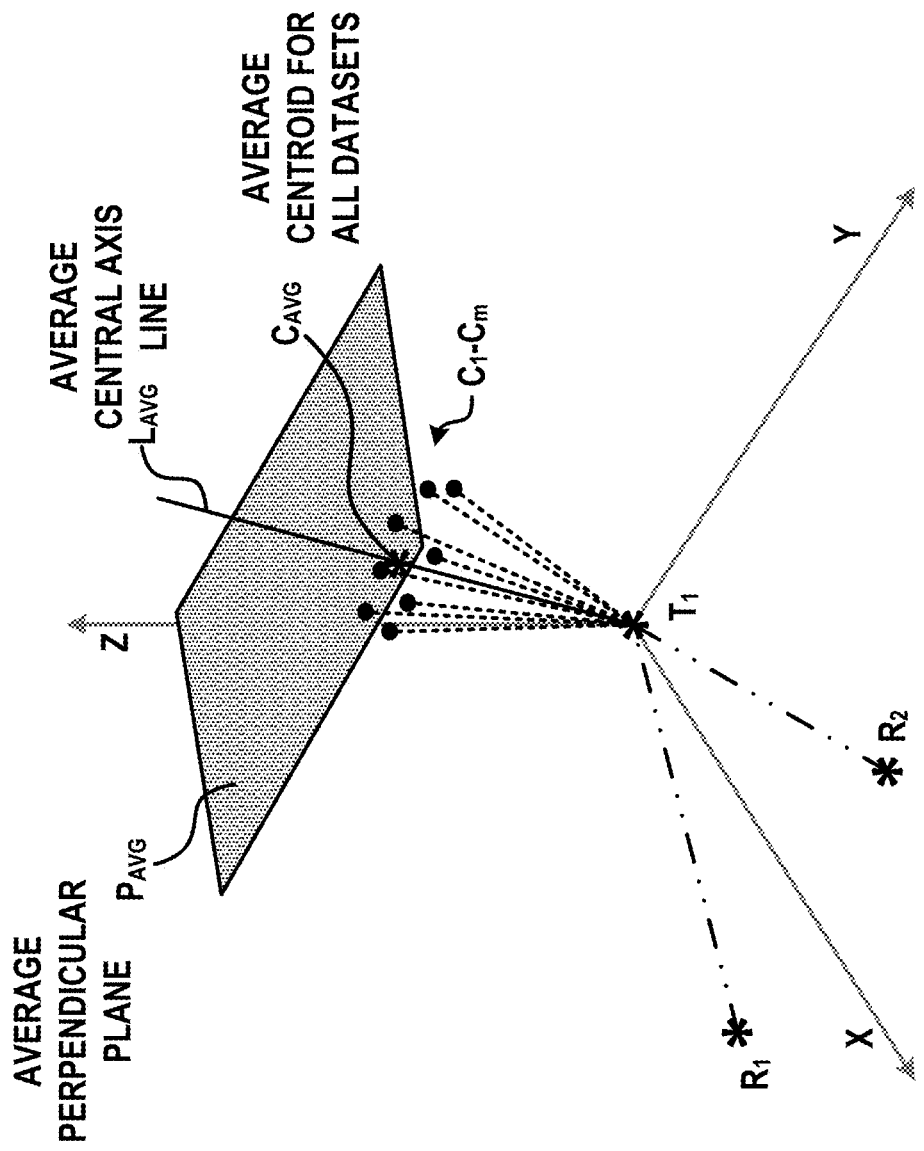
FIG. 8 is a graphical representation showing the measured data points and the second 3D coordinate system of FIG. 5 defining an average perpendicular plane perpendicular to the centroid corridor line of FIG. 7.
Figure 10:
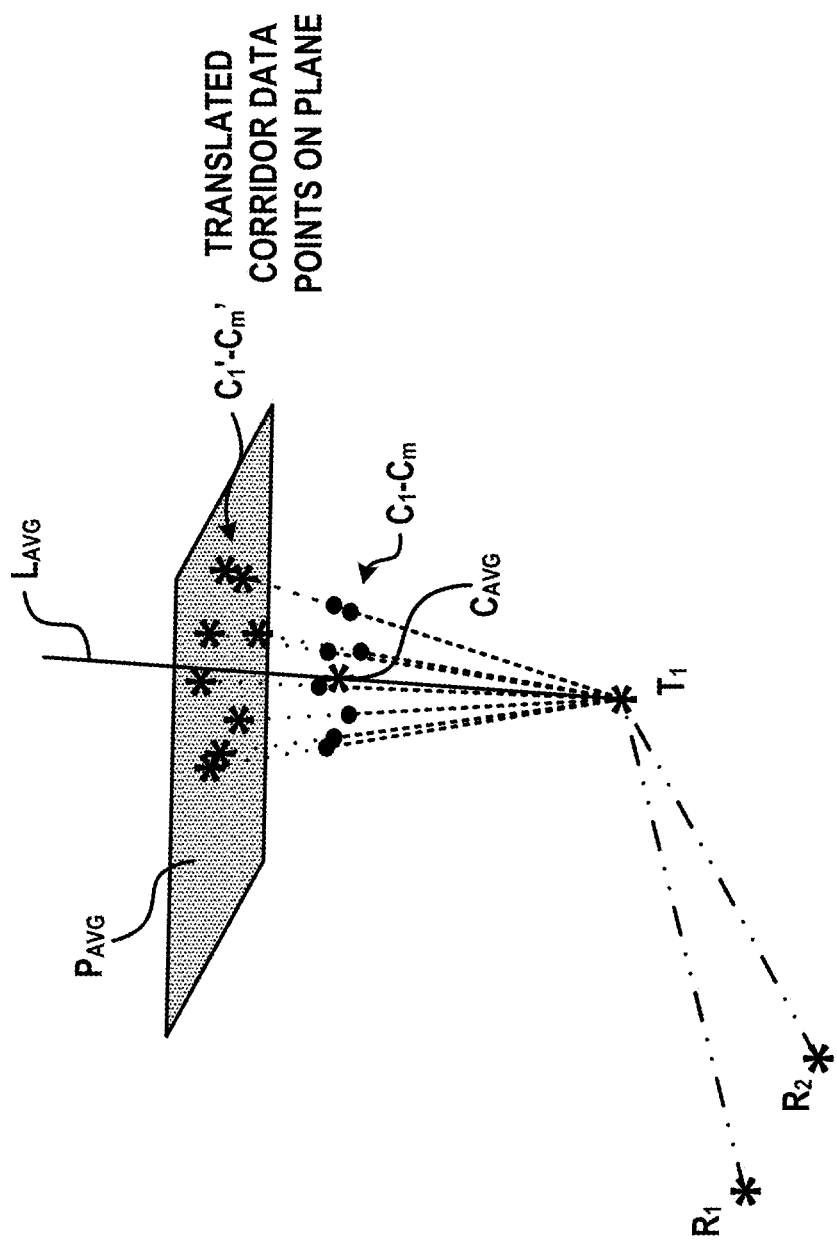
FIG. 10 is a graphical representation showing translation of the plurality of corridor points to the average perpendicular plane of FIG. 8.
Figure 11:
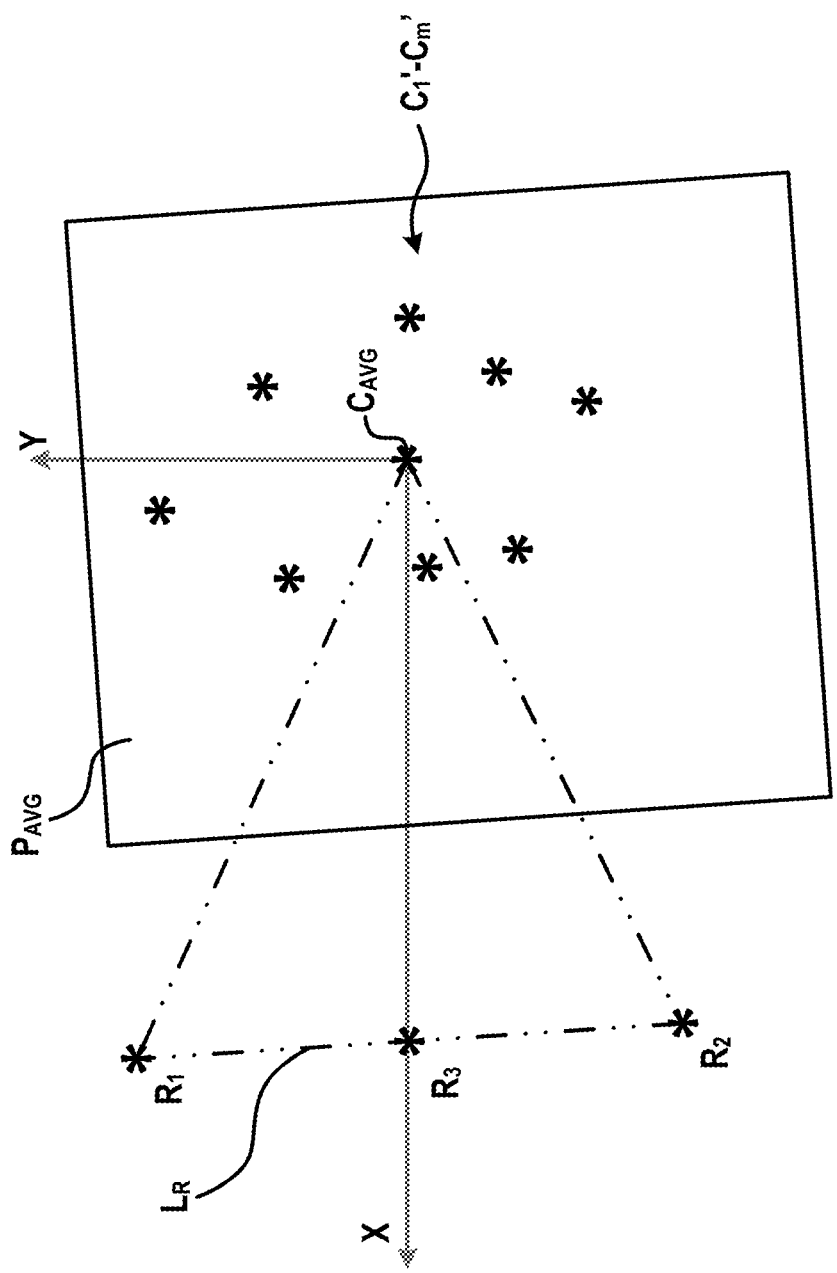
FIG. 11 is a graphical representation showing alignment of a first 2D coordinate system with translated corridor points defined on the average perpendicular plane of FIG. 10.
Figure 13:
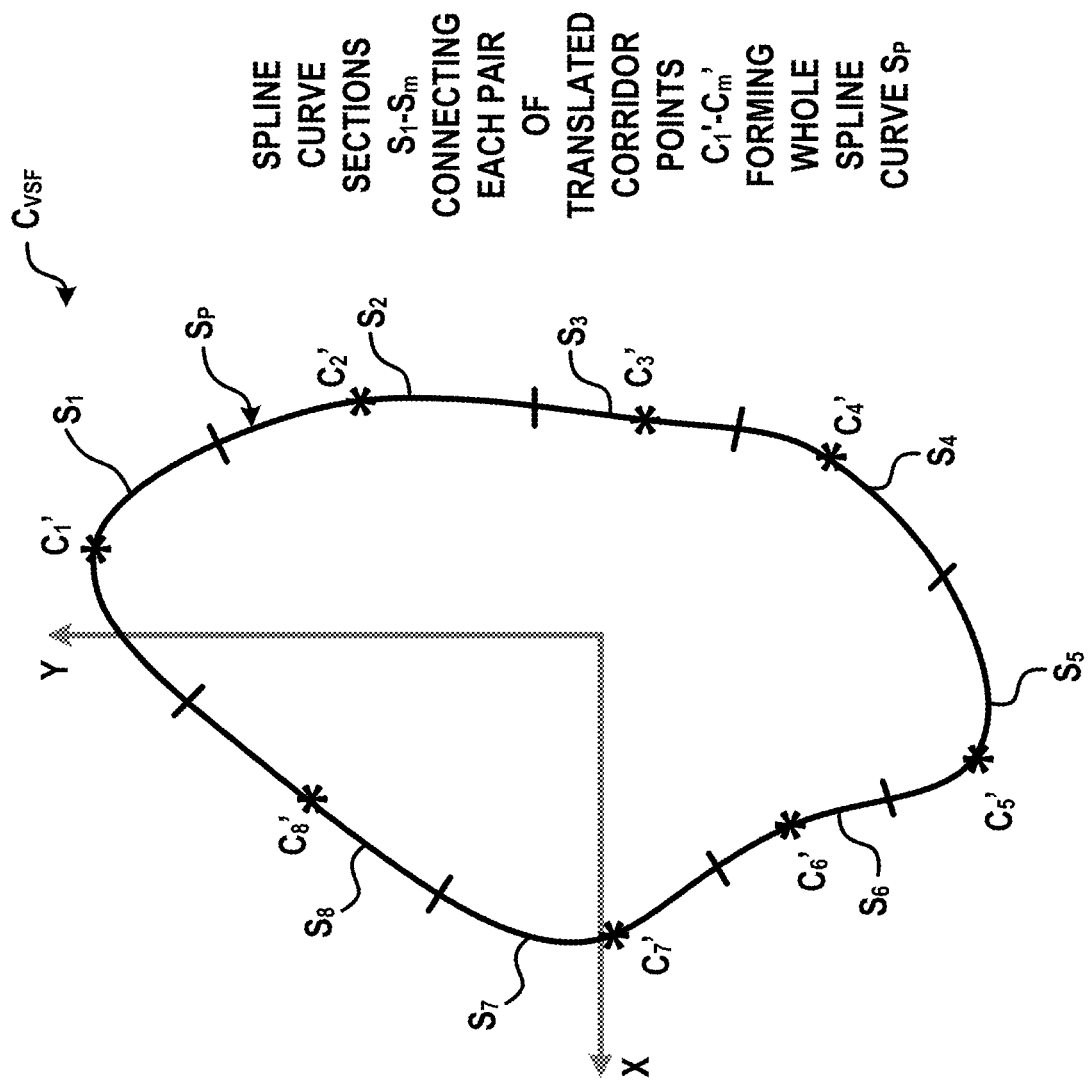
FIG. 13 is a graphical representation showing determination of a plurality of polynomials of spline curves that fit to the plurality of corridor points to determine a shape of a surgical corridor within the first 2D coordinate system of FIG. 11.
Figure 14:
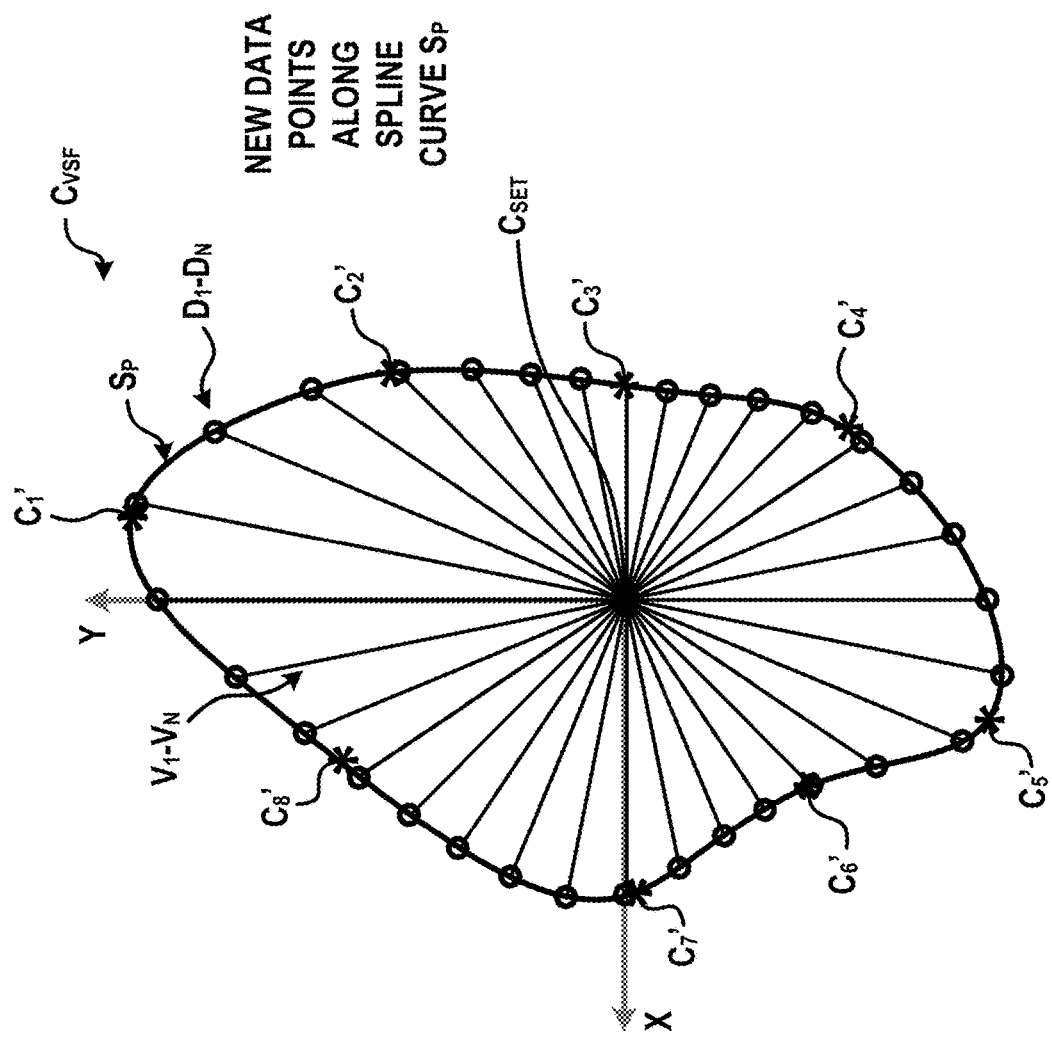
FIG. 14 is a graphical representation showing generation of additional data points along a plurality of radial division lines that fit to the spline curve of FIG. 13.

Referring to FIG. 3 and as further illustrated in FIGS. 4-16, a method 200 is shown for generating an average surgical corridor $C_{VSF\_AVG}$ by the system 100 using sets of measured data points taken from the plurality of selected datasets of the plurality of datasets, each respective dataset of the plurality of datasets corresponding to one specimen of a plurality of specimens. At block 210 of method 200, the process of which is elaborated on in FIGS. 4-6, the system 100 translates the set of measured data points for each selected dataset including 3D positional coordinate data from a first 3D coordinate system to a standardized second 3D coordinate system, including the first reference point $R_1$, the second reference point $R_2$, the target structure reference point $T_1$, and the plurality of original corridor points $C_1$-$C_m$. The second 3D coordinate system is oriented as shown in FIG. 5, however it should be noted that the orientation of the second 3D coordinate system is not limited to this configuration and other orientations of the second 3D coordinate system are also contemplated. At block 220, the process of which is elaborated on in FIGS. 7-9, the system 100 determines a centroid line $L_C$ for each selected dataset of the plurality of selected datasets based on the plurality of original corridor points $C_1$-$C_m$ relative to the target structure $T_1$, and the system 100 further determines an average central axis line $L_{AVG}$ for all of the plurality of selected datasets by averaging together each centroid line $L_C$ of each selected dataset of the plurality of selected datasets. Using average central axis line $L_{AVG}$, the system 100 determines an average perpendicular plane $P_{AVG}$ perpendicular to the average central axis line $L_{AVG}$. In some embodiments, the average perpendicular plane $P_{AVG}$ can be represented at a fixed distance outside of the body to enable projection of the surgical corridor shape to any distance outside the body. At block 230, the process of which is elaborated on in FIGS. 10-12, the system 100 translates the original corridor points $C_1$-$C_m$ for each selected dataset of the plurality of selected datasets to the average perpendicular plane $P_{AVG}$ to provide a plurality of translated corridor points $C_1'$-$C_m'$ for each dataset on a first 2D coordinate system. This allows the system 100 to directly compare data between each respective selected dataset of the plurality of selected datasets since each corridor point is now on a standardized coordinate system. At block 240, the process of which is elaborated on in FIGS. 13-15, the system 100 generates a shape of a surgical corridor $C_{VSF}$ for each selected dataset of the plurality of selected datasets by fitting a spline curve $S_P$ to the translated corridor points $C_1'$-$C_m'$. The system 100 generates additional data points $D_1$-$D_N$ equidistantly along the spline curve $S_P$ to further fill in the surgical corridor $C_{VSF}$. At block 250, further in FIG. 16, the system 100 generates an average surgical corridor $C_{VSF\_AVG}$ based on each outer shape of the surgical corridor $C_{VSF}$ for each respective selected dataset of the plurality of selected datasets collectively described by the translated corridor points $C_1'$-$C_m'$, the additional data points $D_1$-$D_N$ and target structure $T_1$ for each respective dataset. The system 100 can translate the average surgical corridor $C_{VSF\_AVG}$ to a 3D coordinate system. At block 260, the system 100 displays a model of the average surgical corridor $C_{VSF\_AVG}$ superimposed on patient imaging at the appropriate location relative to the target structure and the average plane as shown in FIGS. 18A-18D.

Translation of Data in 3D Space

Referring to FIGS. 3-6, the first step to determine the average surgical corridor is illustrated in block 210 (FIG. 6) of method 200. In a first block 212 of block 210, the system 100 obtains the reference points $R_1$, $R_2$ and $T_1$, as well as original corridor points $C_1$-$C_m$ for each selected dataset of the plurality of selected datasets. At a second block 214 of block 210, the system 100 translates the reference points $R_1$, $R_2$ and $T_1$, as well as original corridor points $C_1$-$C_m$ in 3D space from a first 3D coordinate system to a second 3D coordinate system. An example first 3D coordinate system is illustrated in FIG. 4; translated points are shown in FIG. 5 in the second 3D coordinate system. The purpose of the translation is such that all of the plurality of selected datasets can be aligned in 3D space.

The system 100 places the target structure reference point $T_1$ at the origin of the second 3D coordinate system. Further, the system 100 identifies a reference point $R_3$ as a point midway on a line $L_R$ between the first reference point $R_1$ and the second reference point $R_2$. The system 100 "draws" a line joining reference midpoint $R_3$ to the target structure reference point $T_1$ along the X-axis of the second 3D coordinate system, and places the first and second reference points $R_1$ and $R_2$ on an XY plane of the second 3D coordinate system such that the XY plane intersects all three reference points $R_1$, $R_2$ and $R_3$.

To maintain consistency between all measured datasets, the y coordinate of the first reference point $R_1$ can always be negative, and the y coordinate of the second reference point $R_2$ can always be positive, thus ensuring the model is aligned consistently. It should be noted that for other structures of the body, reference points $R_1$ and $R_2$ can be selected at different landmarks and are not limited to the glabella and lateral canthus; however the landmarks of selected reference points do need to be consistent across all datasets.

Once the system 100 establishes the reference points $R_1$, $R_2$ and $R_3$ of the second 3D coordinate system as in block 212, the system 100 translates the reference points and the original corridor points of each dataset of the plurality of selected datasets to the second 3D coordinate system in block 214.

Calculation of Cone Central Axis Line for Each Dataset

Referring to FIGS. 3 and 7-9, at sub-block 222 of block 220, the system 100 identifies a centroid point $C_{SET}$ of the original corridor points $C_1$-$C_m$ for each selected dataset of the plurality of selected datasets by separately averaging x, y and z coordinates of all the original corridor points $C_1$-$C_m$ for the dataset. The system 100 identifies a central axis line $L_C$ of a cone shape by finding a difference vector between the target structure reference point $T_1$ and the centroid point $C_{SET}$ of the original corridor points $C_1$-$C_m$, where the cone shape is representative of the surgical corridor.

Calculation of an Average Perpendicular Plane

Referring to FIGS. 3 and 7-9, at sub-blocks 224 and 226 of block 220, the system 100 determines an average central axis line $L_{AVG}$ having an average centroid point $C_{AVG}$ across the plurality of selected datasets by averaging x, y and z coefficients for a plurality of central axis lines $L_C$ respectively associated with each centroid point $C_{SET}$ of each respective selected dataset of the plurality of selected datasets. The system 100 can then characterize an average perpendicular plane $P_{AVG}$ for the plurality of selected datasets as a plane for which the average central axis $L_{AVG}$ is the normal vector. The absolute position of the average perpendicular plane $P_{AVG}$ in 3D space is reasonably arbitrary, but the average surgical returned is more useful if the model extends from the target structure reference point $T_1$ to the outside of the skull in all cases, so a fixed length can be selected to ensure this; for example 200 mm. With a fixed distance between the target structure reference point $T_1$ and the average perpendicular plane $P_{AVG}$, the average perpendicular plane $P_{AVG}$ can be fully defined in 3D space.

Translation of the Coordinate Data from Each Dataset to the Average Perpendicular Plane Referring to FIGS. 3 and 10-12, at sub-block 232 of block 230, the system 100 determines a plurality of vectors between the target structure reference point $T_1$ and each original corridor point $C_1$-$C_m$ of each dataset, and calculates the intersection of these vectors with the average perpendicular plane $P_{AVG}$ to translate each original corridor point $C_1$-$C_m$ to the average perpendicular plane $P_{AVG}$. These intersection points are the new translated corridor points $C_1'$-$C_m'$ for each respective selected dataset of the plurality of selected datasets after translation onto the average perpendicular plane $P_{AVG}$ and extending along the same lines between the target structure reference point $T_1$ and the original corridor points $C_1$-$C_m$.

Translation to a 2D Coordinate System

Referring to FIGS. 3 and 10-12, at sub-block 234 of block 230, once the data points have been translated on to the average perpendicular plane $P_{AVG}$ which is standardized, the system 100 can define a first 2D coordinate system on the average perpendicular plane $P_{AVG}$. The orientation of this 2D coordinate system must be very carefully considered and must be consistent for all data points. There are 3 orientation options that the system 100 can use for orienting the axes:

1. Orient the X-axis of the new 2D coordinate system along the projection of the line joining the target structure reference point $T_1$ and the first reference point $R_1$.
2. Orient the X-axis of the new 2D coordinate system along the projection of the line joining the target structure reference point $T_1$ and the second reference point $R_2$.
3. Orient the X-axis of the new 2D coordinate system along the projection of the line joining the target structure reference point $T_1$ and the midpoint $R_3$ between the first reference point $R_1$ and the second reference point $R_2$. This option will most likely prove to be the best option, as the variation in distance between the first reference point $R_1$ and the second reference point $R_2$ will be split evenly between the two sides. In the other two cases, the variation in distance will offset all of the measured data points in one direction.

When the X-axis orientation has been fixed on the average perpendicular plane $P_{AVG}$, the system 100 can easily determine the Y-axis at right angles to the X-axis. If the same calculation method is applied consistently by the system 100, the orientation of the Y-axis will be consistent on the 2D plane. The system 100 can then convert 3D coordinate data of the translated corridor points $C_1'$-$C_m'$ for a selected dataset of the plurality of selected datasets to a 2D coordinate system on the average perpendicular plane $P_{AVG}$. It should be noted that although the average perpendicular plane $P_{AVG}$ is used in this method as the plane on which to create the 2D coordinate system, many other choices of planes could be used. One such example would be to use a plane parallel but offset to the reference plane.

Calculation of the Piecewise Polynomials of Spline Curves for Each Dataset

Referring to FIGS. 3 and 13-15, at sub-block 242 of block 240, the system 100 approximates the shape of the surgical corridor for each selected dataset of the plurality of selected datasets using a piecewise spline curve $S_P$ for each individual dataset. The system 100 generates the piecewise spline curve $S_P$ using the translated data points $C_1'$-$C_m'$ (after translation to the 2D coordinate system) as control points for the piecewise spline curve $S_P$. The system 100 can define a plurality of respective spline curve sections $S_1$-$S_m$ of the piecewise spline curve $S_P$ using separate 3rd degree polynomials. The system 100 can determine the equations for each polynomial making up the spline curve $S_P$ using the following constraints:

The piecewise spline curve $S_P$ intersects all data points $C_1'$-$C_m'$.

A spline curve section $S_m$ between each two points $C_m'$, $C_m-1'$ is governed by a separate cubic polynomial.

For adjacent spline curve sections, the slope of the spline curve sections are the same where the spline curve sections meet at the data points (e.g., first derivatives of the two polynomials are equal).

For adjacent spline curve sections, the curvature is the same where the spline curve sections meet (e.g., second derivatives of the polynomials are equal).

Calculation of Radial Intersection Points

Referring to FIGS. 3 and 13-15, at sub-block 244 of block 240, the system 100 draws radial reference lines $V_1$-$V_N$ at fixed angles from the centroid $C_{SET}$ of the 2D points of each individual dataset, which also corresponds with a relative XY position of the target structure $T_1$. At sub-block 246 of block 240, to calculate an average surgical corridor shape, the system 100 defines a new, larger set of data points $D_1$-$D_N$ along fixed references along the piecewise spline curve $S_P$ for each individual dataset. The fixed references being used are radial reference lines $V_1$-$V_N$. The points of intersection between the reference radial lines $V_1$-$V_N$ and the cubic polynomial of the piecewise spline curve $S_P$ constitute the new set of data points $D_1$-$D_N$ representing the shape of the surgical corridor on the 2D plane. In particular, the system 100 defines an intersection point $D_u$ where $u \in \{1, \ldots, N\}$, where the radial reference line $V_u$ intersects with the piecewise spline curve $S_P$. The polynomial has a check on the result to ensure that the correct polynomial for spline curve section $S_t$ where $t \in \{1, \ldots, m\}$ of the spline curve $S_P$ is being used. After the intersection point $D_u$ has been calculated, the system 100 checks to ensure that the x and y values of the new coordinate $D_u$ fall between the x and y values of the two data points $C_t'$ and $C_r'$ where $t,r \in \{1, \ldots, m\}$ at the limits of the polynomial being calculated. If the new intersection point $D_u$ is outside this range, the intersection $D_u$ with the radial reference line $V_u$ in question is calculated on the next spline curve section of the spline curve $S_P$.

The result of these calculations is that for each radial reference line $V_u$, there will be one intersection point $D_u$ associated with it in each dataset.

Calculation of Average Surgical Corridor on 2D Plane

Figure 16:
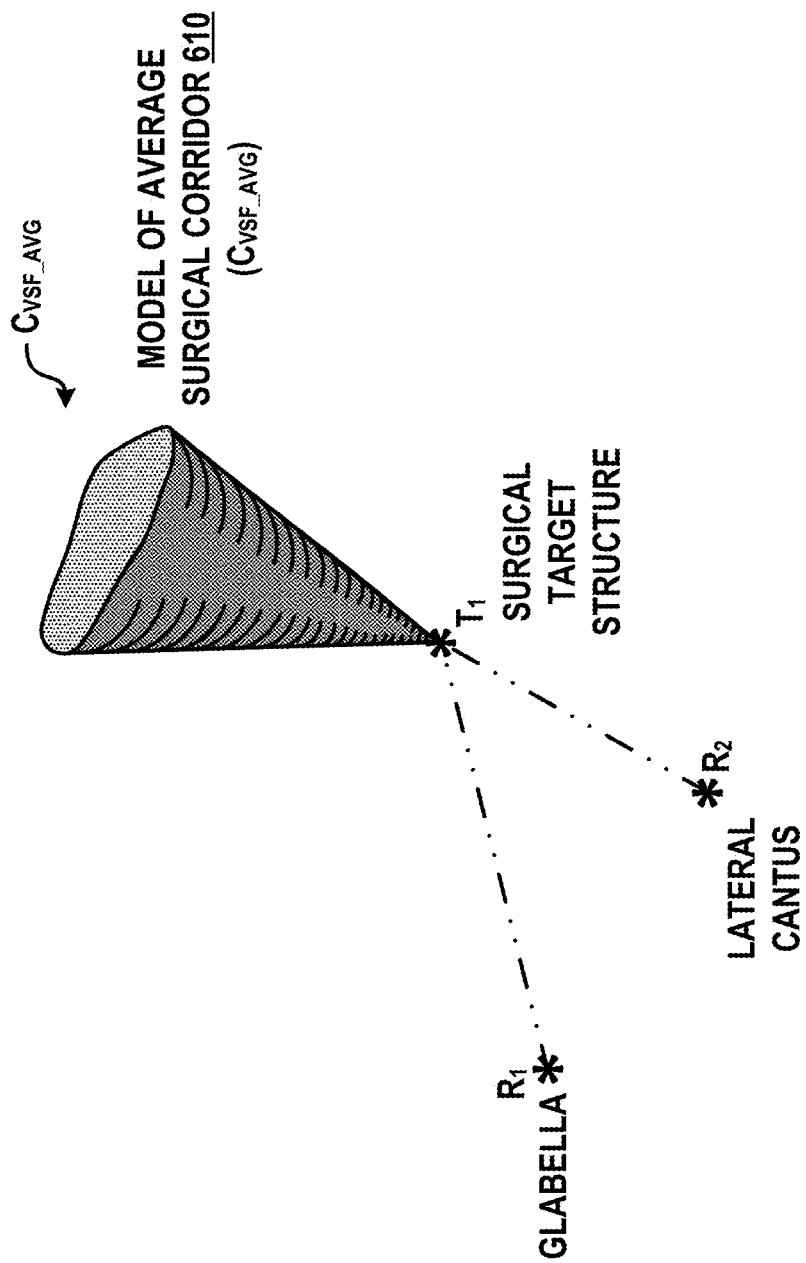
FIG. 16 is a graphical representation showing a sample 3D model representing an output of an average surgical corridor model of the system of FIG. 1A.

Referring to FIGS. 3, 16 and 17, at block 250, the new set of data points $D_1$-$D_N$ for each dataset has been determined from a fixed reference $C_{SET}$ which is common to all datasets, the points are directly comparable. At sub-block 252 of block 240, to determine the average surgical corridor $C_{VSF\_AVG}$ in the 2D coordinate system, for each respective radial reference line $V_u$, the system 100 calculates the averages of the intersection point $D_u$ associated with the radial line $V_u$ on all datasets. This gives a single 2D reference point $D_u$ for each radial reference line $V_u$, and together, these 2D points collectively define the outline of the average surgical corridor $C_{VSF\_AVG}$ that is an average surgical corridor across the plurality of datasets.

Translation of Average Points Back to 3D Space

Referring to block 254 of block 250 of FIG. 17, the target of the method 200 is to produce a model of the average surgical corridor from the selected datasets, so when the data points comprising the average surgical corridor are calculated, they must then be translated back to the global 3D coordinate system. The relationship between the 2D and 3D coordinate systems have been established from the earlier translation in the other direction.

Result

Figure 18A:
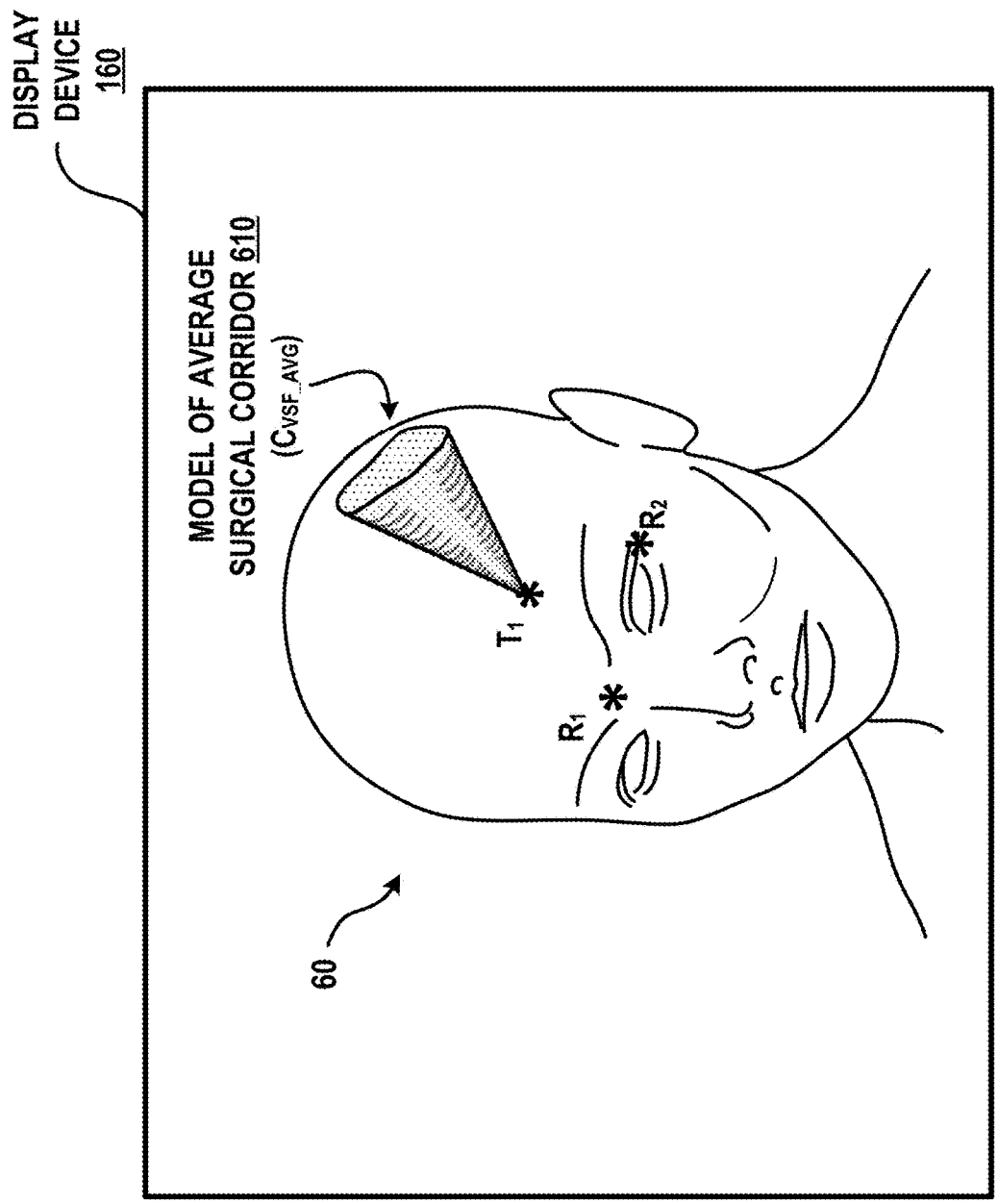
FIGS. 18A-18D are example images showing superposition of a model of the average surgical corridor on patient imaging using the system of FIG. 1A.
Figures 18B, 18C, 18D:
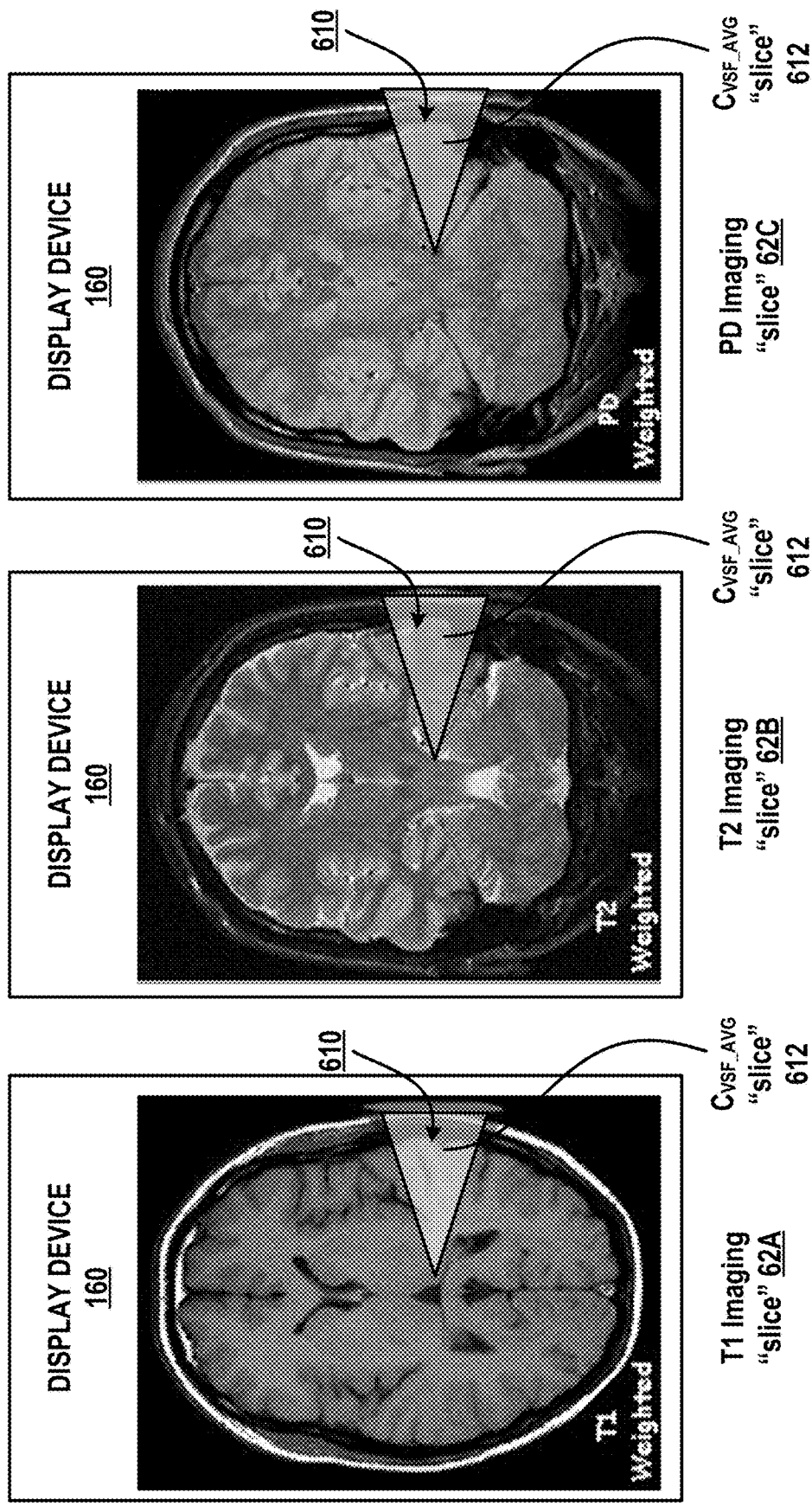

The result of the method 200 is to produce a model 610 of the average surgical corridor $C_{VSF\_AVG}$, shown in FIGS. 16-18D. The model 610 includes at least 3 reference points, the target structure reference point $T_1$, the first reference point $R_1$ and the second reference point $R_2$. In the embodiments of FIGS. 16 and 18A, the model 610 can be a 3D model, and can be aligned over patient imaging and displayed at the display device 160. In some embodiments, patient imaging can be in the form of a 3D patient model 60, which can be created by assembling a plurality of cross-sectional image "slices" into a 3D model. In the embodiment of FIGS. 18B-18D, patient imaging can be represented at the display device 160 as one or more cross-sectional images (collectively, imaging "slices" 62) such as a T1-weighted imaging "slice" 62A, a T2-weighted imaging "slice" 62B, and a PD-weighted imaging "slice" 62C, with a corresponding "slice" 612 of the model 610 positioned where it belongs relative to the imaging "slices" 62 of the patient imaging. With these reference points, the system 100 can align the model 610 with patient imaging in the following ways:

1) Move the model 610 with respect to the patient imaging such that the surgical target structure reference point $T_1$ of the model 610 (e.g., the apex of the cone shape) is coincident with the surgical target structure in patient imaging.
2) Rotate the model 610 to achieve the best alignment of the first reference point $R_1$ and the second reference point $R_2$ associated with the model 610 with their corresponding positions in patient imaging.

In this way, at block 260 of FIG. 3, the system 100 can superimpose the model 610 of the average surgical corridor on patient imaging to produce a combined model of the patient's imaging dataset(s) and an expected surgical corridor.

Method of Use

For a user to interact with the system 100 to generate and use the model of the average surgical corridor, the database 130 that provides the set of measured data points must be available to the user through the user interface 140. FIG. 19 illustrates an overall method 300 by which the system 100, illustrated in FIG. 1A, provides an average surgical corridor to the user.

1) At block 310 of method 300, the system 100 receives a query through the user interface 140 that indicates the following procedural information regarding a surgical procedure to be performed:
   Surgical target structure
   Surgical Approach
   Head Side
   Maneuver
   Laterality
   Visualization Method
2) At block 320 of method 300, the system 100 receives a combination (some or all) of the following patient-specific information regarding the surgical procedure to be performed through the user interface 140:
   Age (number and/or range)
   Sex
   Pathology
   Neuroimaging volumetric (computed tomography or magnetic resonance imaging)/anatomical parameters for example:
   Total Intracranial volume
   Parenchymal volume
      (i) Supratentorial volume
      (ii) Intratentorial volume
   The patient-specific information and procedural information is used by the system 100 to identify one or more similar datasets of the plurality of datasets within the database 130. For instance, a practitioner can enter a query for a patient into the user interface 140 that includes procedural information and patient-specific information so that the system 100 can generate the model of the average surgical corridor (such as model 610 of FIGS. 18A-18D) based on a plurality of selected datasets that fall within an appropriate range of similarity to the patient.
3) At block 330 of method 300, the system 100 queries the database 130 based on the procedural information and the patient-specific information to identify a plurality of selected datasets of a plurality of datasets stored within the database 130. At block 340 of method 300, the system 100 retrieves the plurality of selected datasets from the database 130.
   The system 100 receives a selection of a range or tolerance for each of the patient specific parameters, and searches the database for all datasets which fall within the specified range/tolerance of the patient information.
   The system 100 can have specific tolerances set for each patient specific parameter, and the system 100 searches for all entries within the tolerances.
   The system 100 can have a specified minimum number of entries required to determine the average surgical corridor, and widens or tightens the tolerances to retrieve the specified number of entries from the database. In this way, for a set of parameters for which there exists a lot of data, the entries returned can be within a very tight tolerance of the patient specific parameters, but if there is a scarcity of data, tolerances of the system 100 can be expanded to ensure a minimum number of entries are used to determine the average surgical corridor.
   In some embodiments, a practitioner can review the plurality of selected datasets to accept or reject one or more of the selected datasets of the plurality of selected datasets.
4) At block 350 of method 300, the system 100 calculates the average surgical corridor based on the surgical corridors belonging to the plurality of selected datasets (e.g., using method 200 described herein). At block 360 of method 300, the system 100 returns various metrics including the average normalized volume of the surgical corridors. At block 370 of method 300, the system 100 generates a 3D model such as model 610 of the average surgical corridor.

5) At block 380, the system 100 superimposes the 3D model over patient imaging and aligns the model such that the surgical target structure reference point $T_1$ of the 3D model is coincident with the surgical target structure in the patient imaging, the first reference point of the 3D model is aligned as closely as possible with a corresponding position in the patient imaging, and the second reference point of the 3D model is aligned as closely as possible with a corresponding position in the patient imaging. At block 390, the system 100 displays, at the display device 160, the 3D model of the average surgical corridor with respect to patient imaging. An example of this is shown in FIG. 18A, where the model 610 is a 3D model superimposed over a 3D model 60 representative of patient imaging. In FIGS. 18B-18D, the system 100 can display the model 610 as a slice 612 superimposed over cross-sectional imaging "slices" 62 representative of patient imaging.

In some embodiments, components of surgical corridor modeling system 100 can be at least partially developed as a web application, designed for cloud hosting, and/or accessible to registered users from any web browser.

Database Model

Figure 20:
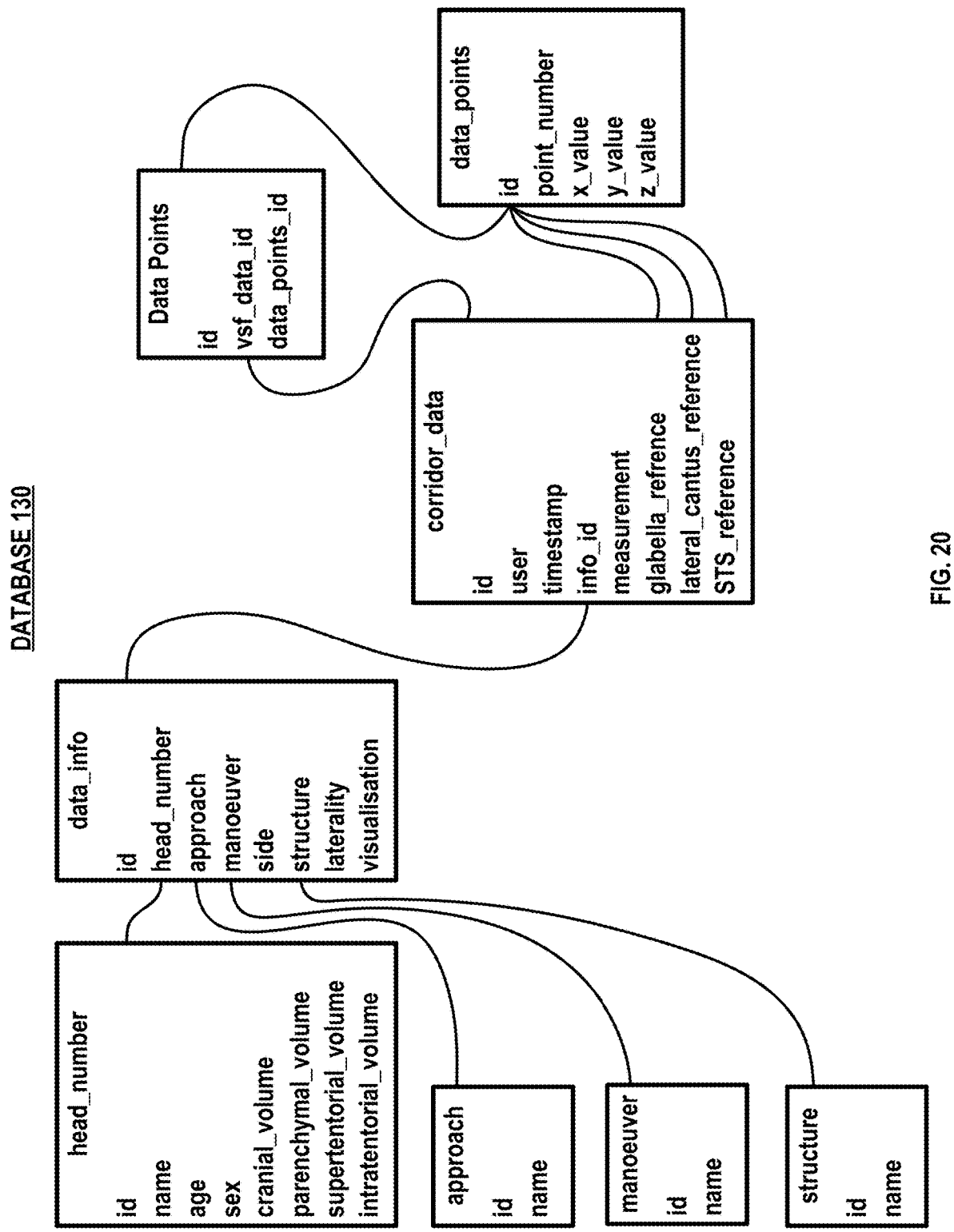
FIG. 20 is a diagram showing a database layout for the system of FIG. 1A.

FIG. 20 illustrates an example database 130 for organizing data within the plurality of datasets for operation of the system 100. To calculate an average surgical corridor model $C_{VSF\_AVG}$, the database 130 needs to be adequately labeled. For a particular embodiment, each dataset in the database 130 requires the following information:

Surgical target structure
Surgical Approach.
Head Side
Unique identifier for head (head number)

In addition, the following data should also be used to distinguish between different datasets:

Manoeuver(s) used during approach
Laterality
Visualization method (endoscope or microscope) a head number:

The following information is required for each head, as identified by

Figure 21:
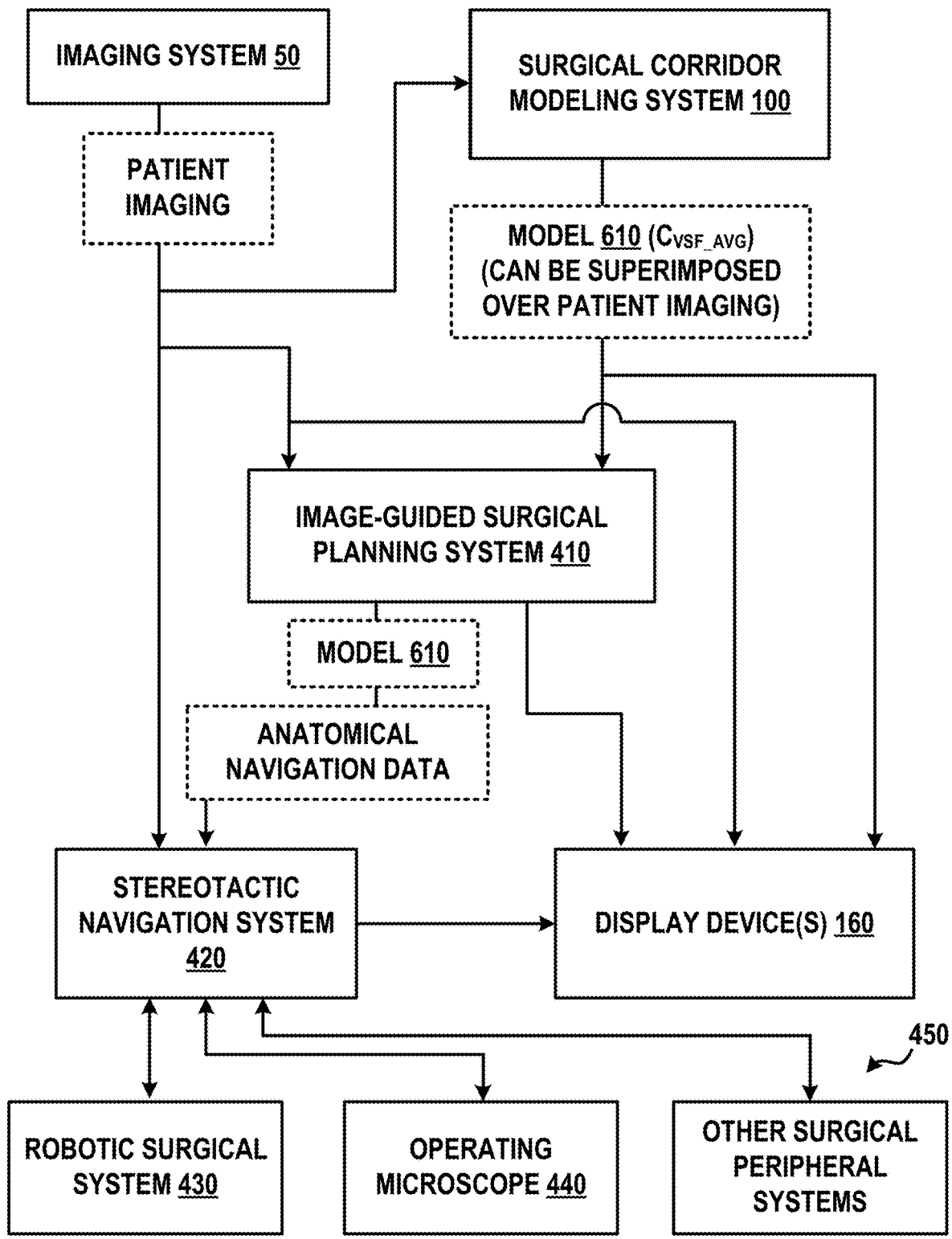
FIG. 21 is a simplified diagram showing integration of the system of FIG. 1A with a surgical assistance environment.
Figure 22A:
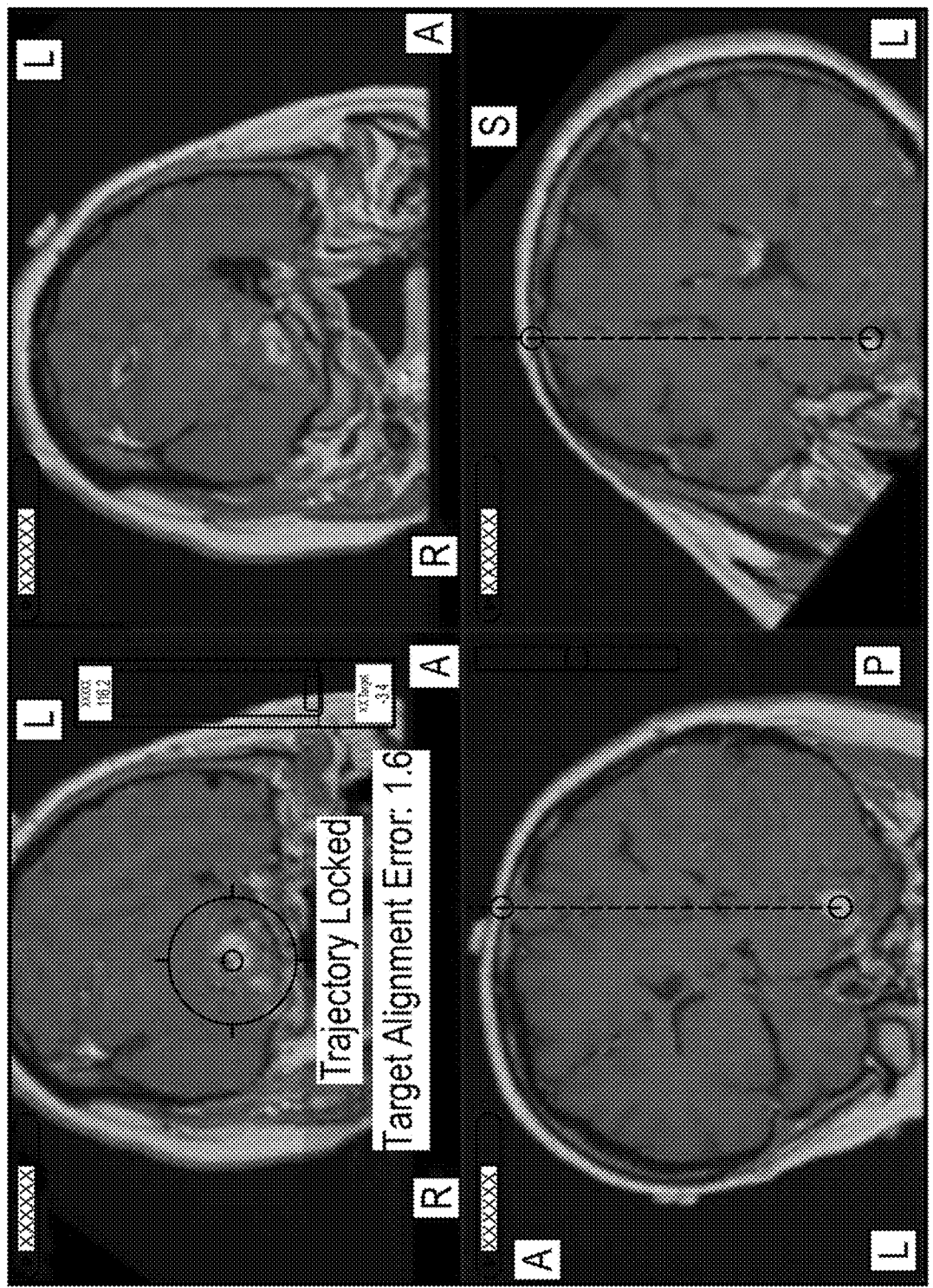
FIGS. 22A and 22B are a pair of images respectively showing an output of a previous image-based surgical planning system and an example output of an image-based surgical planning system of FIG. 21 that incorporates the model of FIG. 18A into the surgical planning environment.
Figure 22B:
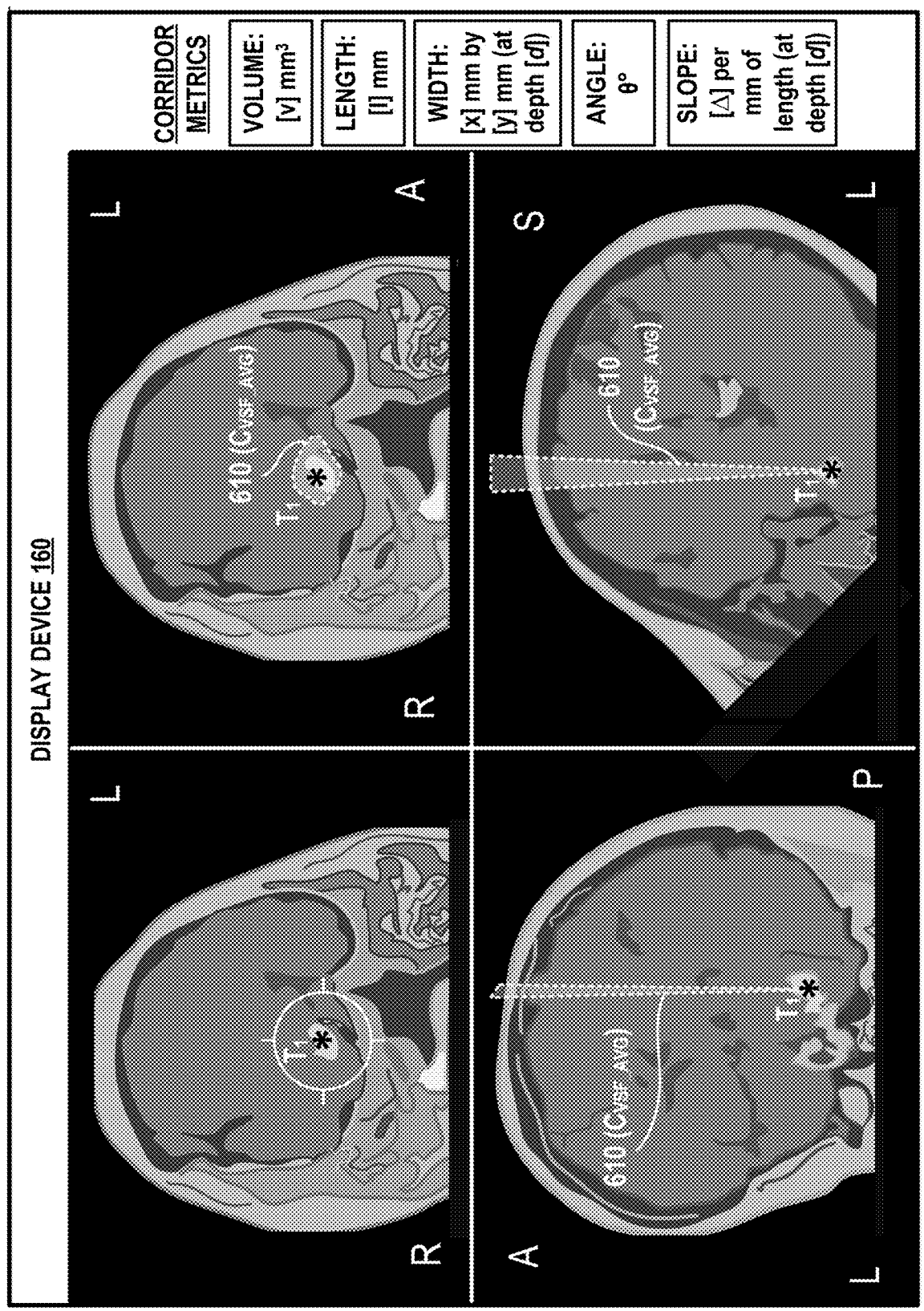

Age
Sex
Total Intracranial Volume
Parenchymal Volume
  Supratentorial volume
  Infratentorial volume Surgical System Integration FIG. 21 illustrates an example surgical assistance environment 400 that incorporates the surgical corridor modeling system 100 to provide practitioners with helpful volumetric information about a surgical corridor during a surgical case. As shown, the surgical assistance environment 400 can incorporate the surgical corridor modeling system 100 with an image-guided surgical planning system 410 for preoperative planning and can further include a stereotactic navigation system 420 for intra-operative navigation. In the example shown, the surgical corridor modeling system 100 can receive patient imaging from an imaging system 50, such as a magnetic resonance imaging system or another imaging modality, and can superimpose the model 610 of the average surgical corridor $C_{VSF\_AVG}$ over patient imaging. The model 610 can be displayed at display device 160 along with patient imaging. The surgical corridor modeling system 100 can further communicate the model 610 of the average surgical corridor $C_{VSF\_AVG}$ to the image-guided surgical planning system 410 for pre-operative planning and stereotactic registration. With reference to FIG. 22A, current image-guided surgical planning technologies show trajectories by simple lines on the display that point to the surgical target structure, sometimes including metrics such as distances and lengths. In contrast, with reference to FIG. 22B, the image-guided surgical planning system 410 can display the model 610 indicative of the average surgical corridor over patient imaging at the display device 160 that provides a volume or an otherwise more informative volumetric trajectory that renders a surgical approach shape and/or volume of the surgical workspace, rather than simple lines. Further, in some embodiments, the image-guided surgical planning system 410 can display various corridor metrics related to the model 610 at the display device 160 to provide quantitative information to practitioners such as allowable working volume, approach angle, etc. In the example shown, corridor metrics can include but are not limited to a total volume, a total length, an expected corridor width (which can vary by depth below a surface), an approach angle, and/or a slope of the corridor (e.g., how sharply the corridor narrows as the corridor approaches the surgical target structure, which can vary by depth relative to the surface). In some embodiments, the image-guided surgical planning system 410 can incorporate assessments of a plurality of possible surgical corridors enabled by different surgical approaches to aid a practitioner in selecting an optimal surgical approach. For instance, the image-guided surgical planning system 410 can display a plurality of models such as model 610 superimposed over patient imaging along with corridor metrics for each model of the plurality of models. In some embodiments, the image-guided surgical planning system 410 can "highlight" approaches that have certain features, such as approaches having a maximal or minimal allowable working volume, a shortest corridor length, that avoid restricted areas, that have a reduced or minimal risk factor, etc. As such, incorporating the model 610 generated by the surgical corridor modeling system 100 with the image-guided surgical planning system 410 can enable a practitioner to make informed decisions when planning a surgical case.

In some embodiments, the image-guided surgical planning system 410 can communicate the model 610 along with anatomical navigation data to the stereotactic navigation system 420 for integration of the model 610 into the surgical workflow. During a surgical case, the stereotactic navigation system 420 can aid a practitioner with navigating the surgical workspace and can provide information related to positions and orientations of various surgical instruments and/or surgical tracking devices relative to the surgical workspace (such as an operating microscope or stereotactic markers). The stereotactic navigation system 420 can incorporate the model 610 into the surgical workflow by providing positions and orientations of instruments and other objects relative to the corridor outlined by the model 610. For instance, the stereotactic navigation system 420 can register patient anatomy within a virtual space S, which can be a 3D virtual space indicative of the real surgical workspace. The stereotactic navigation system 420 can further define a volumetric range of a surgical corridor using the model 610 which can have a volumetric range ($<x_{m1}, x_{m2}>$, $<y_{m1}, y_{m2}>$, $<z_{m1}, z_{m2}>$)$\in$S within the virtual space S. Further, the stereotactic navigation system 420 can track positions of objects such as surgical instruments, stereotactic markers, or anatomical structures (e.g., generically, a position $P=(x_P, y_P, z_P)\in S$). By defining the volumetric range of the model 610 in the same virtual space as registered patient anatomy, and by defining the positions of various objects such as surgical instruments, stereotactic markers, or anatomical structures in the same virtual space, the stereotactic navigation system 420 can provide helpful navigational information to practitioners especially in terms of the allowable working volume of the average surgical corridor indicated by the model 610. The stereotactic navigation system 420 can display this information including the model 610 and patient imaging at the display device 160, the model 610 being indicative of a volumetric trajectory of a surgical approach. Further, in some embodiments, the stereotactic navigation system 420 can use the model 610 as provided by the surgical corridor modeling system 100 to initially estimate the surgical corridor and can update the model 610 as needed through observation of the surgical corridor in practice. In another aspect, the stereotactic navigation system 420 can monitor a position of a surgical instrument relative to the surgical corridor indicated by the model 610 to ensure that the surgical instrument does not exit the surgical corridor, and can provide one or more warnings, alerts or indications to a practitioner when the stereotactic navigation system 420 detects such an event.

Further, in some embodiments, the stereotactic navigation system 420 can communicate the model 610 to various surgical peripheral systems 450 such as a robotic surgical system 430 and/or an operating microscope 440. In one example, the robotic surgical system 430 can receive the model 610 provided by the surgical corridor modeling system 100 as guidance for an expected surgical operating space, the model 610 being indicative of a volumetric trajectory of a surgical approach. In another example, the stereotactic navigation system 420 can receive video data of the surgical workspace from the operating microscope 440 and can display the video data from the operating microscope 440 at the display device 160 with reference to the model 610 indicative of the surgical corridor to further aid the practitioner when navigating the surgical workspace.

Computer-Implemented System

Figure 23:
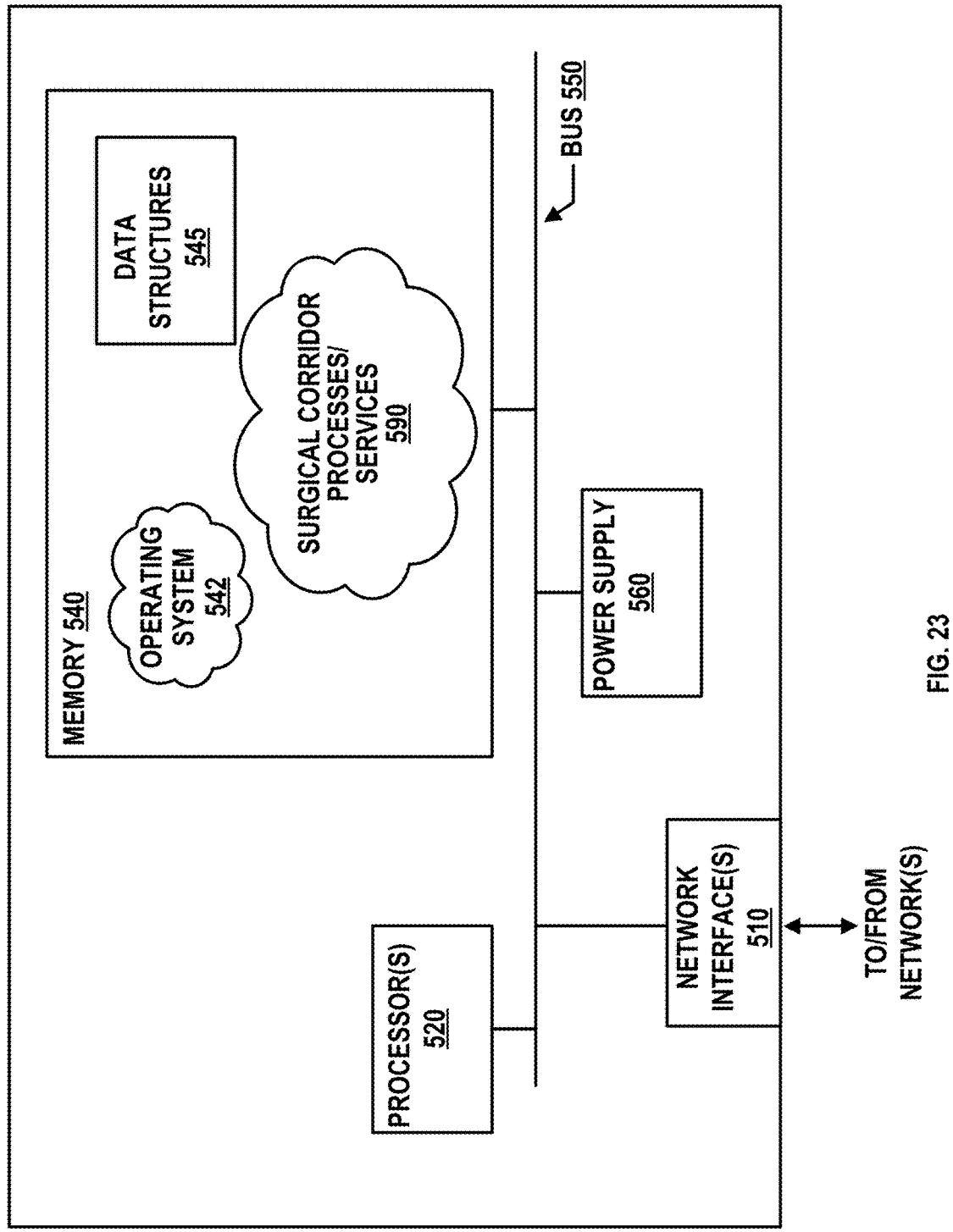
FIG. 23 is a simplified diagram showing an exemplary computing system for implementation of the system of FIG. 1A.

FIG. 23 is a schematic block diagram of an example device 500 that may be used with one or more embodiments described herein, e.g., as a component of surgical corridor modeling system 100 or as a component of surgical assistance environment 400.

Device 500 includes one or more network interfaces 510 (e.g., wired, wireless, PLC, etc.), at least one processor 520, and a memory 540 interconnected by a system bus 550, as well as a power supply 560 (e.g., battery, plug-in, etc.).

Network interface(s) 510 include the mechanical, electrical, and signaling circuitry for communicating data over the communication links coupled to a communication network. Network interfaces 510 are configured to transmit and/or receive data using a variety of different communication protocols. As illustrated, the box representing network interfaces 510 is shown for simplicity, and it is appreciated that such interfaces may represent different types of network connections such as wireless and wired (physical) connections. Network interfaces 510 are shown separately from power supply 560; however, it is appreciated that the interfaces that support PLC protocols may communicate through power supply 560 and/or may be an integral component coupled to power supply 560.

Memory 540 comprises a plurality of storage locations that are addressable by processor 520 and network interfaces 510 for storing software programs and data structures associated with the embodiments described herein. In some embodiments, device 500 may have limited memory or no memory (e.g., no memory for storage other than for programs/processes operating on the device and associated caches).

Processor 520 comprises hardware elements or logic adapted to execute the software programs (e.g., instructions) and manipulate data structures 545. An operating system 542, portions of which are typically resident in memory 540 and executed by the processor, functionally organizes device 500 by, inter alia, invoking operations in support of software processes and/or services executing on the device. These software processes and/or services may comprise surgical corridor process/services 590, described herein as average surgical corridor processes/services 120 and methods 200 and 300. Note that while surgical corridor modeling process/services 590 is illustrated in centralized memory 540, alternative embodiments provide for the process to be operated within the network interfaces 510, such as a component of a MAC layer, and/or as part of a distributed computing network environment.

It will be apparent to those skilled in the art that other processor and memory types, including various computer-readable media, may be used to store and execute program instructions pertaining to the techniques described herein. Also, while the description illustrates various processes, it is expressly contemplated that various processes may be embodied as modules or engines configured to operate in accordance with the techniques herein (e.g., according to the functionality of a similar process). In this context, the term module and engine may be interchangeable. In general, the term module or engine refers to model or an organization of interrelated software components/functions. Further, while the surgical corridor modeling processes/services 590 is shown as a standalone process, those skilled in the art will appreciate that this process may be executed as a routine or module within other processes.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

The invention claimed is:

1. A system, comprising:
    a probe configured to extract a set of measured data points;
    a processor in communication with the probe and a memory, the memory including instructions, which, when executed, cause the processor to:
        obtain the set of measured data points for a selected dataset of a plurality of selected datasets, the set of measured data points including a first reference point, a second reference point, a target structure reference point, and a plurality of corridor points, the set of measured data points defined within a first 3D coordinate system;
        determine an average central axis line and an associated average perpendicular plane for the plurality of selected datasets based on the set of measured data points;
        translate, by the processor, the set of measured data points for each selected dataset of the plurality of selected datasets from the first 3D coordinate system to a standardized second 3D coordinate system;
        translate the plurality of corridor points associated with each respective selected dataset of the plurality of selected datasets to the average perpendicular plane to generate a plurality of translated corridor points associated with each respective selected dataset of the plurality of selected datasets;

generate a plurality of corridor intersection points that fit a spline curve for each respective selected dataset of the plurality of selected datasets, the spline curve being fit to the plurality of translated corridor points; and generate an average surgical corridor by averaging a shape of a surgical corridor and a target structure for each selected dataset of the plurality of selected datasets, wherein the surgical corridor is determined for each selected dataset using corridor intersection points of the plurality of corridor intersection points at equidistance radial vector;

a display in communication with the processor and configured to display a model average surgical corridor superimposed over patient imaging for more accurate surgical corridor modeling.

2. The system of claim 1, wherein the memory includes instructions, which, when executed, further cause the processor to:

determine, by the processor, a centroid line between the plurality of corridor points and the target structure for each selected dataset of the plurality of selected datasets;

determine, by the processor, the average central axis line for the plurality of selected datasets based on the centroid line associated with each respective selected dataset and the target structure; and determine, by the processor, the average perpendicular plane that is perpendicular to the average central axis line at a distance from the target structure.

3. The system of claim 2, wherein the memory includes instructions, which, when executed, further cause the processor to:

record a corridor intersection point of the plurality of corridor intersection points at an intersection of the spline curve and a radial vector of a plurality of radial vectors, wherein each respective radial vector starts at the centroid line and crosses the spline curve.

4. The system of claim 1, wherein the memory includes instructions, which, when executed, further cause the processor to:

align, at the processor, the model indicative of the average surgical corridor over the patient imaging.

5. The system of claim 4, wherein the memory includes instructions, which, when executed, further cause the processor to:

generate, at the processor, a 3D version of the model indicative of the average surgical corridor.

6. The system of claim 1, further comprising:

a probe in operative communication with the processor and/or the memory, the probe being configured to extract the set of measured data points for recordation by the processor and/or the memory.

7. The system of claim 6, wherein the memory includes instructions, which, when executed, further cause the processor to:

measure, by the probe, the first reference point at a first location on a body; and measure, by the probe, the second reference point at a second location on the body.

8. The system of claim 6, wherein the memory includes instructions, which, when executed, further cause the processor to:

measure, by the probe, the target structure reference point at the target structure within a body.

9. The system of claim 6, wherein the memory includes instructions, which, when executed, further cause the processor to:

measure, by the probe, the plurality of corridor points at an extrema of a physical surgical corridor within a body.

* * * * *